(12) United States Patent
Fiset

(10) Patent No.: US 10,881,284 B2
(45) Date of Patent: Jan. 5, 2021

(54) SCOPE CLEANING DEVICE CONFIGURED TO BE REMOVEABLY CONNECTED TO A SURGICAL TOOL

(71) Applicant: Medix3d LLC, Santa Monica, CA (US)

(72) Inventor: Claude Fiset, Ojai, CA (US)

(73) Assignee: Medix3d LLC, Corona del Mar, CA (US)

( * ) Notice: Subject to any disclaimer, the term of this patent is extended or adjusted under 35 U.S.C. 154(b) by 0 days.

(21) Appl. No.: 16/288,914

(22) Filed: Feb. 28, 2019

(65) Prior Publication Data

US 2019/0191982 A1 Jun. 27, 2019

Related U.S. Application Data

(63) Continuation-in-part of application No. 16/110,035, filed on Aug. 23, 2018, now Pat. No. 10,575,722, which is a continuation of application No. 14/966,622, filed on Dec. 11, 2015, now Pat. No. 10,080,488.

(60) Provisional application No. 62/091,466, filed on Dec. 12, 2014.

(51) Int. Cl.
| | |
|---|---|
| *A61B 1/04* | (2006.01) |
| *A61B 1/12* | (2006.01) |
| *A61B 17/34* | (2006.01) |
| *A61B 1/313* | (2006.01) |
| *A61B 1/00* | (2006.01) |
| A61B 90/70 | (2016.01) |

(52) U.S. Cl.
CPC ............ *A61B 1/126* (2013.01); *A61B 1/0014* (2013.01); *A61B 1/121* (2013.01); *A61B 1/127* (2013.01); *A61B 1/313* (2013.01); *A61B 17/3417* (2013.01); *A61B 2090/701* (2016.02)

(58) Field of Classification Search
CPC ................................ A61B 1/126; A61B 1/127
USPC ................................. 600/104, 133, 157, 169
See application file for complete search history.

(56) References Cited

U.S. PATENT DOCUMENTS

| | | |
|---|---|---|
| 4,392,485 A | 7/1983 | Hiltebrandt |
| 5,382,297 A | 1/1995 | Valentine et al. |
| 5,910,106 A | 6/1999 | Morgan et al. |
| 5,993,379 A | 11/1999 | Ouchi et al. |
| 6,503,192 B1 | 1/2003 | Ouchi |
| 7,080,641 B2 | 7/2006 | Gomez |
| 7,179,223 B2 | 2/2007 | Motoki et al. |
| 7,198,599 B2 | 4/2007 | Goto et al. |
| 7,311,660 B2 | 12/2007 | Gomez |
| 7,803,109 B2 | 9/2010 | Gomez |

(Continued)

*Primary Examiner* — Matthew J Kasztejna
(74) *Attorney, Agent, or Firm* — The Webb Law Firm

(57) ABSTRACT

A cleaning device for a surgical tool includes a housing having at least one opening for accessing an interior of the housing; a sponge and a heater assembly positioned in the interior of the housing; and a connector. The connector includes a first arm and a second arm extending from an outer surface of the housing. An inner surface of the first arm and an inner surface of the second arm define at least a first recess sized to receive a sidewall of a first tubular body having a first diameter, and a second recess sized to receive a sidewall of a second tubular body having a second diameter, different than the first diameter. The connector is configured to removably attach the housing to the sidewall of the first tubular body or to the sidewall of the second tubular body to supporting the housing relative to the tubular body.

20 Claims, 23 Drawing Sheets

(56) References Cited

U.S. PATENT DOCUMENTS

| | | |
|---|---|---|
| 7,922,650 B2 | 4/2011 | McWeeney et al. |
| 7,927,330 B2 | 4/2011 | Platt |
| 7,955,330 B2 | 6/2011 | Platt |
| 8,148,667 B2 | 4/2012 | Faries, Jr. et al. |
| 8,152,717 B2 | 4/2012 | Gomez |
| 8,185,997 B2 | 5/2012 | Heck |
| 8,353,815 B2 | 1/2013 | Okada |
| 8,452,068 B2 | 5/2013 | Averbuch et al. |
| 8,454,645 B2 | 6/2013 | Criscuolo et al. |
| 8,467,589 B2 | 6/2013 | Averbuch et al. |
| 8,517,918 B2 | 8/2013 | Smith |
| 8,535,220 B2 | 9/2013 | Mondschein |
| 8,540,745 B2 | 9/2013 | Criscuolo et al. |
| 8,696,552 B2 | 4/2014 | Whitman |
| 8,721,529 B2 | 5/2014 | Hess et al. |
| 8,727,969 B2 | 5/2014 | Leiner |
| 8,870,752 B2 | 10/2014 | Avitsian et al. |
| 9,060,676 B2 | 6/2015 | Blackhurst et al. |
| 9,078,694 B2 | 7/2015 | Hartoumbekis et al. |
| 2002/0022762 A1 | 2/2002 | Beane et al. |
| 2005/0234295 A1 | 10/2005 | Gomez |
| 2007/0142702 A1* | 6/2007 | Haller .................. A61B 1/313 600/102 |
| 2008/0277853 A1* | 11/2008 | Menn .................. A61B 1/0014 269/87 |
| 2010/0168520 A1 | 7/2010 | Poll et al. |
| 2012/0184897 A1 | 7/2012 | Poll |
| 2012/0197084 A1 | 8/2012 | Drach et al. |
| 2013/0060086 A1 | 3/2013 | Talbert et al. |
| 2016/0135673 A1 | 5/2016 | Miller et al. |
| 2019/0053966 A1 | 2/2019 | Pigazzi |

\* cited by examiner

SCOPE CLEANING DEVICE CONFIGURED TO BE REMOVEABLY CONNECTED TO A SURGICAL TOOL

CROSS REFERENCE TO RELATED APPLICATIONS

The present application is a continuation-in-part of U.S. patent application Ser. No. 16/110,035, filed Aug. 23, 2018, which is a continuation of U.S. patent application Ser. No. 14/966,622, filed Dec. 11, 2015, which claims priority to U.S. Provisional Patent Application No. 62/091,466, filed on Dec. 12, 2014, each of which is hereby incorporated by reference in its entirety.

BACKGROUND

Field

The present application relates to a cleaning device for cleaning a scope, laparoscope, or microscope used in surgery or other medical procedures, and a method of using the device during surgical or other medical procedures. The present application further relates to a cleaning kit for cleaning a trocar and a scope, laparoscope, or microscope used in surgery or other medical procedures, and a method of using the kit during surgical or other medical procedures.

Description of the Related Art

The following patents and patent publications are hereby incorporated by reference: U.S. Patent Application Publication No. 2012/0184897, having the title "INTEGRATED SYSTEMS AND METHODS FOR MAINTENANCE AND MANAGEMENT OF AN INTRA-ABDOMINAL GAS ENVIRONMENT DURING LAPAROSCOPIC SURGERY," published Jul. 19, 2012; U.S. Patent Application Publication No. 2012/0197084, having the title "SYSTEMS AND METHODS FOR OPTIMIZING AND MAINTAINING VISUALIZATION OF A SURGICAL FIELD DURING THE USE OF SURGICAL SCOPES," published Aug. 2, 2012; U.S. Patent Application Publication No. 2013/0060086, having the title "IMAGING SENSOR PROVIDING IMPROVED VISUALIZATION FOR SURGICAL SCOPES," published on Mar. 7, 2013; U.S. Patent Application Publication No. 2010/0168520, having the title "VIEW OPTIMIZER AND STABILIZER FOR USE WITH SURGICAL SCOPES," published Jul. 1, 2010; U.S. Pat. No. 8,535,220, having the title "LAPAROSCOPE CLEANING SYSTEM," issued Sep. 17, 2013; U.S. Pat. No. 4,392,485, having the title "ENDOSCOPE," issued on Jul. 12, 1983; U.S. Pat. No. 8,152,717, entitled "DEVICE FOR WHITE BALANCING AND APPLYING AN ANTI-FOG AGENT TO MEDICAL VIDEOSCOPES PRIOR TO MEDICAL PROCEDURES," issued on Apr. 10, 2012; U.S. Pat. No. 7,803,109, entitled "METHOD AND APPARATUS FOR PROTECTING THE DISTAL LENS OF ENDOSCOPES," issued on Sep. 28, 2010; U.S. Pat. No. 7,311,660, entitled "METHOD AND APPARATUS FOR HEATING AND APPLYING WARM ANTIFOG SOLUTION TO ENDOSCOPES AS WELL AS A DISTAL LENS PROTECTOR," issued on Dec. 25, 2007; U.S. Pat. No. 7,080,641, entitled "METHOD AND APPARATUS FOR HEATING STERILE SOLUTIONS DURING MEDICAL PROCEDURES," issued on Jul. 25, 2006; U.S. Pat. No. 8,870,752, entitled "MEDICAL DEVICE SHEATH," issued on Oct. 28, 2014; U.S. Pat. No. 8,727,969, entitled "ENDOSCOPE," issued on May 20, 2014; U.S. Pat. No. 8,696,552, entitled "SELF-CONTAINED STERILIZABLE SURGICAL SYSTEM," issued on Apr. 15, 2014; U.S. Pat. No. 8,540,745, entitled "BALLOON DISSECTOR WITH CANNULA," issued on Sep. 24, 2013; U.S. Pat. No. 8,517,918, entitled "OPTICAL TROCAR WITH SCOPE HOLDING ASSEMBLY," issued on Aug. 27, 2013; U.S. Pat. No. 8,467,589, entitled "HYBRID REGISTRATION METHOD," issued on Jun. 18, 2013; U.S. Pat. No. 8,454,645, entitled "BALLOON DISSECTOR WITH CANNULA," issued on Jun. 4, 2013; U.S. Pat. No. 8,452,068, entitled "HYBRID REGISTRATION METHOD," issued on May 28, 2013; U.S. Pat. No. 7,955,330, entitled "MULTI-PORT SIDE-FIRE COAGULATOR," issued Jun. 7, 2011; and U.S. Pat. No. 7,927,330, entitled "MULTI-PORT SIDE-FIRE COAGULATOR," issued Apr. 19, 2011.

During minimally invasive surgeries, such as laparoscopic surgery, trocars are used to permit access into a patient's body. Trocars are medical devices or instruments that comprise hollow tubes or hollow portions. During surgery, such as laparoscopic surgery, a trocar may be inserted through an incision into a patient's body, such as into the abdominal or pelvic cavity of a patient. The trocar acts as a passageway for other surgical tools or devices, such as scopes, laparoscopes, microscopes, knives, graspers, scissors, staplers, and more, to enter the body for use during surgery.

During such surgical procedures, the lenses of viewing devices inserted into the body through the trocar, such as scopes, laparoscopes, and/or microscopes, may become clouded or the view therethrough may become partially or completely obscured. The view can be obscured, either partially or completely, if the lenses are smeared with bodily fluids or the like, or if the lenses become clouded or fogged over due to the humidity within the body of the patient. In addition, the interior of the trocars should also be kept clean.

An object of the present application may be to provide a cleaning device for a trocar and surgical scopes, which cleaning device may be utilized during surgery. The cleaning device also may be used to defog lenses or optics of a surgical scope.

SUMMARY

When minimally invasive surgeries are performed using trocars, the scopes and/or microscopes used during surgery, which often are inserted into the body of the patient, may become smeared with bodily fluids or the like. This may cause the lens of the scope or microscope to become obscured or clouded because of smearing and/or the humidity or moisture within the body of the patient. Embodiments of the cleaning device and method described herein address these problems. There may be other applications for the scope or microscope, which create the same problems as with minimally invasive surgery, and embodiments of the device and method described below may be appropriate to address those problems as well.

An embodiment of the cleaning device according to the present application may be configured for cleaning a surgical scope during minimally invasive surgery. The cleaning device may comprise a casing which houses a sponge and a heating element, and an attachment element connected to an outer surface of the casing and configured to removably attach the casing to the trocar, wherein the casing is configured to allow a lens of the surgical scope to access the sponge and the heating element. In an embodiment, the casing may comprise a first depression formed in an upper surface of the casing and configured to receive the sponge therein, and a second depression formed in an upper surface of the casing and configured to receive the heating element therein. In an embodiment, the sponge may be impregnated with a cleaning medium. In an embodiment, the cleaning device may include a snap member that is configured to removably attach the casing to the trocar.

In an embodiment, the heating element may be comprised of a heating coil and at least one battery operatively connected to the heating coil, wherein the heating coil is configured to warm the lens of the surgical scope when the surgical scope is positioned in proximity to the heating coil. In an embodiment, the cleaning device may further comprise at least one light operatively connected to the at least one battery.

In an embodiment, the heating element may be comprised of a chemical pack.

An embodiment of the cleaning device described herein may comprise a cover and a wiping element, wherein the cover is disposed over the second depression, wherein the cover comprises a first hole, wherein a wiping element comprises a second hole, and wherein the wiping element is disposed over the cover so that the first hole and the second hole are oriented to allow the surgical scope to access the heating element. In an embodiment, the wiping element may be comprised of a microfiber material.

Another embodiment disclosed herein is a cleaning kit for use during minimally invasive surgery comprising a container housing a sponge and configured to removably attach to the trocar; a cover comprising a scope access hole configured to permit a surgical scope to access the sponge; the cover positioned on an upper surface of the container; and a cannula cleaner comprising an elongated body having a first end having a cleaning tip disposed thereon and a second end, the cannula cleaner configured to be removably supported by at least one of the container and cover when not in use, wherein the cannula cleaner is configured for insertion in a cannula of a trocar and the cleaning tip is configured to contact the cannula when the cannula cleaner is inserted into the cannula. An embodiment of the cleaning kit may include a cannula cleaner wherein the elongated body further comprises a solution container configured to receive a cleaning medium, and a valve disposed on the second end of the elongated body, wherein the valve is configured to dispense the cleaning medium during surgery. In an embodiment, the cleaning kit may comprise at least one wiping element disposed on the cover, wherein the at least one wiping element is configured to allow the surgical scope to access the sponge through the scope access hole. In an embodiment, the cleaning kit may further comprise a snap member configured to attach the container to the trocar.

In an embodiment, the cleaning kit may further comprise a heater disposed in the container, wherein the heater is configured to warm the surgical scope inserted through the scope access hole. In an embodiment, the heater is configured to border a substantial portion of a perimeter of the sponge. In an embodiment, the heater comprises a heating coil and at least one battery operatively connected to the heating coil, and the heating coil is configured to warm the lens of the surgical scope during surgery. In an embodiment, the heater may comprise a chemical pack.

In an embodiment, the cleaning kit may further comprise one or more lights operatively connected to at least one battery.

Another embodiment is directed to a method of cleaning a surgical scope during minimally invasive surgery comprising inserting a trocar into a patient, attaching a cleaning device to the trocar, heating a heating element of the cleaning device to a desired temperature, inserting the surgical scope into the trocar, removing the surgical scope from the trocar, wiping the lens of the surgical scope on the wiping element, and heating the lens of the surgical scope with the heating element. In an embodiment, this method further may comprise wiping the lens on the sponge.

One feature or aspect of an embodiment is using a cleaning device for cleaning laparoscopes used in a medical procedure, the cleaning device comprising a body with a snap device attached to the body, which snap device is configured to attach to a trocar. The body comprises an isosceles triangular shape with a longer side connecting the equal sides of the isosceles triangle with the snap device being attached to the middle of said longer side of the isosceles triangle, and the body comprising two hollowed out portions, one of said hollowed out portions being disposed on each side of said snap arrangement. A first hollowed out portion being configured to house a sponge impregnated with a cleaning solution, which cleaning solution is configured to clean off the tip portion of a laparoscope, where a lens is disposed, which tip portion is configured to be inserted into the trocar and into the body of the patient. A second hollowed out portion being configured to house a heating arrangement, which heating arrangement comprises a chemical heat pack and/or a battery-operated electric heating arrangement and a cover for the heating arrangement being disposed to form a closing side of said second hollowed out portion and being configured to provide an enclosure for the heating arrangement disposed in said second hollowed out portion. The cover comprising at least one of: a heat chamber cover; a microfiber holder; and a microfiber covering layer. The cover further comprises a hole therein being configured to receive a tip of a laparoscope. The procedure comprising: wetting said sponge by impregnating said sponge with cleaning solution, and disposing said impregnated sponge in said first hollowed out portion of said cleaning device; inserting said heating arrangement in said second hollowed out portion of said cleaning device; snapping said cleaning device onto the trocar and orienting said cleaning device toward a surgeon such that the apex of said isosceles triangle is disposed towards the surgeon or in some other direction than the apex being disposed towards said surgeon; heating the heating arrangement to a predetermined temperature; initially inserting a laparoscope into the trocar and into the body of a patient; proceeding with surgery until the lens portion of the laparoscope at its tip becomes smeared with the patient's bodily components or until the lens of the laparoscope is unusable because of condensation on the lens; removing the laparoscope from the trocar and wiping the lens on said impregnated sponge until the bodily components or condensate has been removed; inserting the tip of the laparoscope with its lens through said hole in said heat chamber cover; raising the temperature of the laparoscope tip sufficiently to minimize condensation on the laparoscope lens during a next phase of the surgical procedure; removing the tip of the laparoscope from said heating chamber and inserting the tip of the laparoscope into the trocar; continuing the surgical procedure with a cleaned laparoscope; and repeating the above cleaning operation when required.

Another feature or aspect of an embodiment is a cleaning device for cleaning laparoscopes during a medical procedure for performing laparoscopic surgery, said cleaning device comprising a body with a snap device attached to said body, which snap device is configured to attach to a trocar. The body comprises an isosceles triangular shape with a longer side connecting the equal sides of the isosceles triangle with the snap device being attached to the middle of said longer side of the isosceles triangle and the body comprising two hollowed out portions, one of said hollowed out portions being disposed on each side of said snap arrangement. A first hollowed out portion being configured to house a sponge impregnated with a cleaning solution, which cleaning solution is configured to clean off the tip portion of a laparoscope, where a lens is disposed, which tip portion is configured to be inserted into the trocar and into the body of the patient. A second hollowed out portion being configured to house a heating arrangement, which heating arrangement comprises a chemical heat pack and/or a battery-operated electric heating arrangement and a cover for the heating arrangement being disposed to form a closing side of said second hollowed out portion and being configured to provide an enclosure for the heating arrangement disposed in said second hollowed out portion. The cover comprising at least one of: a heat chamber cover; a microfiber holder; and a microfiber covering layer. The cover further comprises a hole therein being configured to receive a tip of a laparoscope.

According to another embodiment, a cleaning device configured for cleaning a surgical tool prior to insertion of the tool into a body of a patient during minimally invasive surgery includes a housing having at least one opening for accessing an interior of the housing; a sponge and a heater assembly positioned in the interior of the housing; and a connector. The connector includes a first arm and a second arm extending from an outer surface of the housing. An inner surface of the first arm and an inner surface of the second arm define at least a first recess sized to receive a sidewall of a first tubular body having a first diameter, and a second recess sized to receive a sidewall of a second tubular body having a second diameter, different than the first diameter. The connector is configured to removably attach the housing to the sidewall of the first tubular body or to the sidewall of the second tubular body, thereby supporting the housing relative to the first tubular body or the second tubular body.

According to another embodiment, a trocar assembly for introducing a surgical scope to a body during a minimally invasive surgery includes: a trocar having a tubular body with a sidewall having a first maximum outer diameter; and a cleaning device configured to removably mount to the sidewall of the tubular body of the trocar. The cleaning device includes: a housing having at least one opening for accessing an interior of the housing; a sponge and a heater assembly positioned in the interior of the housing; and a connector. The connector includes a first arm and a second arm extending from an outer surface of the housing. An inner surface of the first arm and an inner surface of the second arm define at least a first recess sized to receive the sidewall of the tubular body of the trocar and a second recess sized to receive a sidewall of a tubular body of a trocar having a second diameter which is smaller than the first diameter. The connector is configured to removably attach the housing to the trocar to support the housing relative to the trocar.

According to another embodiment, a cleaning device configured for cleaning a surgical tool prior to insertion of the tool into a body of a patient during minimally invasive surgery includes a trocar and a cleaning portion. The trocar includes a first end configured to remain external to the patient's body, a second end configured for insertion into the patient's body, and a sidewall extending therebetween. The cleaning portion includes: a housing, at least a portion of which is integral with the sidewall of the trocar; a fluid container accessible through at least one first opening of the housing; and a heater assembly for warming a fluid in the container.

Examples of the present invention will now be described in the following numbered clauses:

Clause 1: A cleaning device configured for cleaning a surgical tool prior to insertion of the tool into a body of a patient during minimally invasive surgery, the cleaning device comprising: a housing comprising at least one opening for accessing an interior of the housing; a sponge and a heater assembly positioned in the interior of the housing; and a connector comprising a first arm and a second arm extending from an outer surface of the housing, wherein an inner surface of the first arm and an inner surface of the second arm define at least a first recess sized to receive a sidewall of a first tubular body having a first diameter, and a second recess sized to receive a sidewall of a second tubular body having a second diameter, different than the first diameter, and wherein the connector is configured to removably attach the housing to the sidewall of the first tubular body or to the sidewall of the second tubular body, thereby supporting the housing relative to the first tubular body or the second tubular body.

Clause 2: The cleaning device of clause 1, wherein the tubular body comprises a tubular portion of a surgical trocar.

Clause 3: The cleaning device of clause 1 or clause 2, wherein the connector supports the housing, such that a central longitudinal axis of a portion of the first tubular body received within the first recess or of the second tubular body received within the second recess of the connector is spaced apart from the interior of the housing.

Clause 4: The cleaning device of any of clauses 1 to 3, wherein the connector supports the housing, such that a line normal to a bottom surface and passing through the opening of the housing is parallel to and a fixed distance from a central longitudinal axis of the portion of the first tubular body received within the first recess or of the second tubular body received within the second recess of the connector.

Clause 5: The cleaning device of any of clauses 1 to 4, wherein the at least one opening is sized such that a lens of the surgical tool can be inserted through the at least one opening to access the sponge and/or the heater assembly.

Clause 6: The cleaning device of any of clauses 1 to 5, wherein the first arm and the second arm of the connector are configured to deflect radially outwardly from the first recess and/or the second recess to receive the first or second tubular body and to move radially inwardly to engage a portion of a sidewall of the first or second tubular body upon insertion of the tubular body into the first recess and/or the second recess.

Clause 7: The cleaning device of any of clauses 1 to 6, wherein the first arm and the second arm comprise a first end mounted to a portion of an outer surface of the housing and a free second end opposite the first end, the free second end comprising a protrusion comprising an inwardly angled outer surface configured to direct the sidewall of the first or second tubular body into the first recess and/or the second recess.

Clause 8: The cleaning device of clause 7, wherein an inwardly facing surface of the protrusion is configured to engage the sidewall of the first tubular body of the first diameter to maintain the first tubular body within the first recess.

Clause 9: The cleaning device of clause 7 or clause 8, wherein the first recess is accessible through a space between the protrusion of the first arm and the protrusion of the second arm, and wherein the second recess is accessible from the first recess through a space between portions of the first arm and the second arm other than the protrusions.

Clause 10: The cleaning device of any of clauses 1 to 9, wherein the first diameter is from about 6.0 mm to about 18.0 mm and the second diameter is from about 1.0 mm to about 6.0 mm.

Clause 11: The cleaning device of any of clauses 1 to 10, wherein an inner surface of the first arm and an inner surface of the second arm each comprise a first curved portion having a first radius sized such that the first curved portion engages a sidewall of the first tubular body, and a second curved portion having a radius sized such that the second curved portion engages a sidewall of the second tubular body.

Clause 12: The cleaning device of any of clauses 1 to 11, wherein the first arm and/or the second arm further define at least one third recess sized to receive and engage a sidewall of a third tubular body having a third diameter, which is less than the first diameter or the second diameter, and wherein the third recess is accessible through a space between the inner surface of the first arm and the inner surface of the second arm which forms a portion of the second recess.

Clause 13: The cleaning device of any of clauses 1 to 12, wherein portions of the first arm and/or the second arm configured to contact a sidewall of the first tubular body and/or the second tubular body comprise textured regions configured to enhance a frictional engagement between the sidewall of the tubular body and the inner surface of the first arm and/or the second arm.

Clause 14: The cleaning device of clause 13, wherein the textured regions comprise a plurality of longitudinally extending ribs extending radially inwardly from inner surfaces of the first arm and/or the second arm.

Clause 15: The cleaning device of any of clauses 1 to 14, further comprising a cloth wiping element adhered to a portion of an outer surface of the housing for wiping fluid from a lens of the surgical tool.

Clause 16: The cleaning device of any of clauses 1 to 15, wherein the housing comprises: a base integrally formed with the connector; a cover comprising an open bottom connected to the base, a partially closed top, and an annular sidewall extending therebetween, wherein the at least one opening of the housing extends through the top of the cover; and a tubular fluid reservoir comprising an open top accessible through the at least one opening of the cover and a closed bottom mounted to the base.

Clause 17: The cleaning device of clause 16, wherein the at least one sponge is held in an interior of the fluid reservoir by a frictional engagement between an inner sidewall of the fluid reservoir and an outer annular surface of the at least one sponge.

Clause 18: The cleaning device of clause 16, wherein the heater assembly comprises a conductive film wrapped around at least a portion of a sidewall of the fluid reservoir; an insulating film wrapped around at least a portion of the conductive film of the conductive film; and a thermostat electrically connected between the conductive film and a power source, configured to disconnect the conductive film from the power source when the thermostat measures a temperature above a target value.

Clause 19: The cleaning device of any of clauses 16 to 18, wherein the base further comprises at least one battery terminal, configured to receive at least one battery for powering the heater assembly, and wherein the battery terminal holds the battery in a position, in which a longitudinal axis of the battery is parallel to a longitudinal axis of a portion of the tubular body received by the connector.

Clause 20: A trocar assembly for introducing a surgical scope to a body during a minimally invasive surgery, the assembly comprising: a trocar comprising a tubular body comprising a sidewall having a first maximum outer diameter; and a cleaning device configured to removably mount to the sidewall of the tubular body of the trocar, the cleaning device comprising: a housing comprising at least one opening for accessing an interior of the housing; a sponge and a heater assembly positioned in the interior of the housing; and a connector comprising a first arm and a second arm extending from an outer surface of the housing, wherein an inner surface of the first arm and an inner surface of the second arm define at least a first recess sized to receive the sidewall of the tubular body of the trocar, and a second recess sized to receive a sidewall of a tubular body of a trocar having a second diameter which is smaller than the first diameter, and wherein the connector is configured to removably attach the housing to the trocar to support the housing relative to the trocar.

Clause 21: A cleaning device configured for cleaning a surgical tool prior to insertion of the tool into a body of a patient during minimally invasive surgery, the device comprising: a trocar comprising a first end configured to remain external to the patient's body, a second end configured for insertion into the patient's body, and a sidewall extending therebetween; and a cleaning portion comprising: a housing, at least a portion of which is integral with the sidewall of the trocar; a fluid container accessible through at least one first opening of the housing; and a heater assembly for warming a fluid in the container.

Clause 22: The cleaning device of clause 21, wherein the cleaning portion further comprises an access portion integral with and extending from the first end of the trocar, wherein the access portion is accessible through at least one second opening of the housing.

Clause 23: The cleaning device of clause 22, wherein the access portion comprises a funnel having a first end defined by the at least one second opening of the housing and a narrow second end extending from the first end of the trocar.

Clause 24: The cleaning device of any of clauses 21-23, wherein a central longitudinal axis of trocar is spaced apart from a central longitudinal axis of the fluid container.

Clause 25: The cleaning device of any of clauses 21-24, further comprising at least one sponge disposed in the fluid container.

Clause 26: The cleaning device of clause 25, wherein the at least one sponge is retained in the fluid container by a frictional engagement between an inner sidewall of the fluid container and an outer annular surface of the at least one sponge.

Clause 27: The cleaning device of any of clauses 21-26, wherein the heater assembly comprises a conductive film wrapped around at least a portion of a sidewall of the fluid container.

Clause 28: The cleaning device of clause 27, wherein the heater assembly further comprises an insulating film wrapped around at least a portion of the conductive film and a thermostat electrically connected between the conductive film and a power source, configured to disconnect the conductive film from the power source when the thermostat measures a temperature above a target value.

Clause 29: The cleaning device of any of clauses 21-28, wherein the at least one first opening of the housing is sized such that a lens of the surgical tool can be inserted through the at least one opening to access fluid contained in the fluid container.

Clause 30: The cleaning device of any of clauses 21-29, wherein a minimum outer diameter of the trocar ranges from about 4.0 cm to 8.0 cm.

Clause 31: The cleaning device of any of clauses 21-30, further comprising at least one cloth wiping element adhered to a portion of an outer surface of the housing for wiping fluid from a lens of the surgical tool.

Clause 32: The cleaning device of any of clauses 21-31, further comprising at least one battery terminal positioned in an interior of the housing configured to receive at least one battery for powering the heater assembly, wherein the battery terminal holds the battery in a position, in which a longitudinal axis of the battery is parallel to a longitudinal axis of the trocar.

Clause 33: The cleaning device of any of clauses 21-32, further comprising a first battery terminal positioned in the housing configured to receive a first battery and a second battery terminal positioned in the housing configured to receive a second battery.

Clause 34: The cleaning device of clause 33, wherein the first battery terminal and the second battery terminal are equidistant from a central longitudinal axis of the fluid container.

Clause 35: The cleaning device of clause 34, wherein the first battery terminal and the second battery terminal are symmetrically spaced relative to a vertical plane passing though the trocar and fluid container.

DETAILED DESCRIPTION

Figure 1:
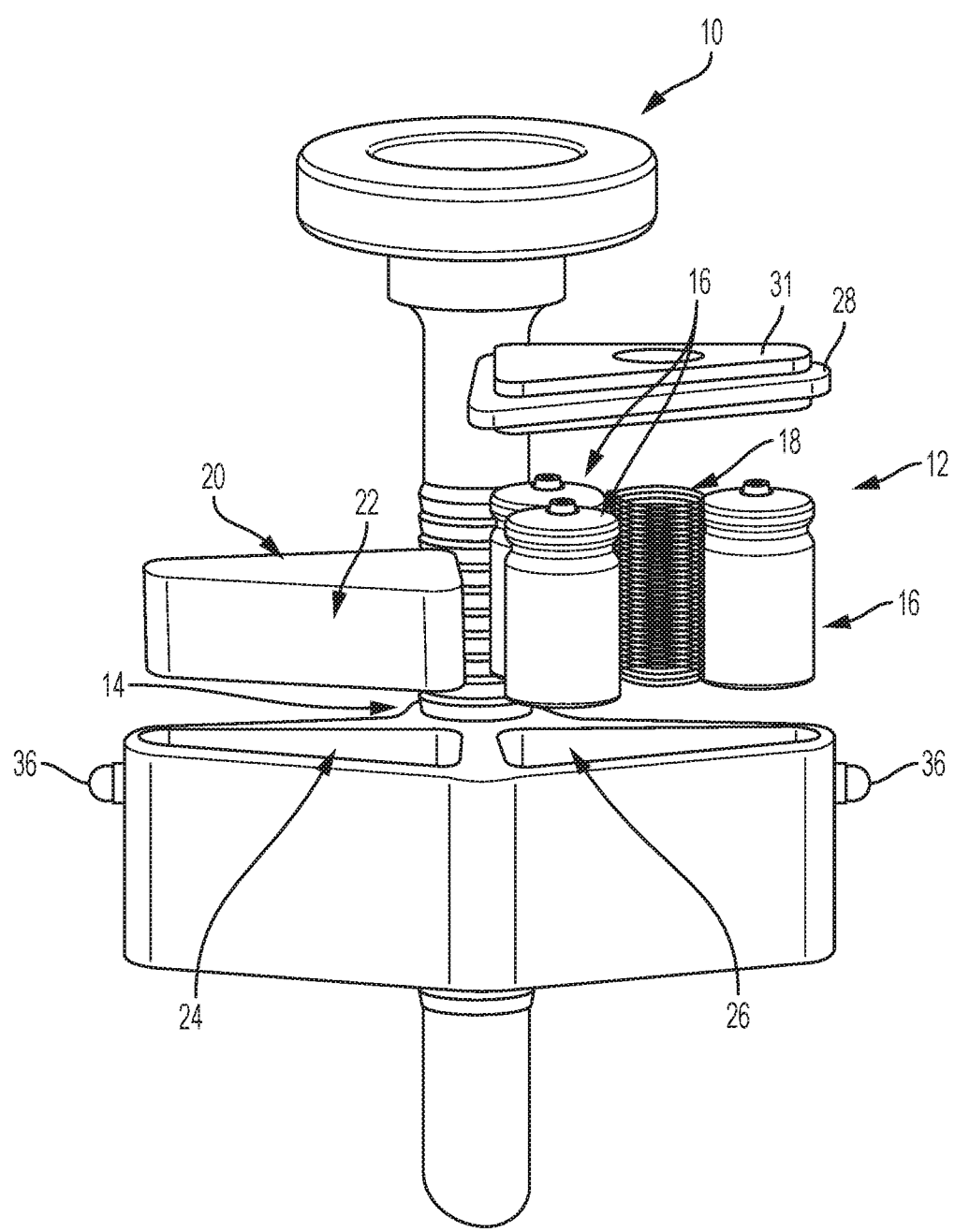
FIG. 1 shows an exploded front view of an embodiment of a cleaning device and a trocar used in at least minimally invasive surgery.

For purposes of the description hereinafter, the spatial orientation terms and derivatives thereof shall relate to the embodiment as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments. Hence, specific dimensions and other physical characteristics related to the embodiments disclosed herein are not to be considered as limiting.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation an object, the term "proximal" refers to portions of the device nearest to a center or center of mass of the object. The term "distal" refers to a portion of the object farthest away from the center or center of mass of the device. For example, for a scope cleaning device, portions of the device located in the interior of the device housing are "proximal" relative to portions of the device connected to and extending from an outer surface of the device housing. When used in connection with a tool, such as a surgical or medical device, such as a surgical scope or trocar, the term "proximal" refers to the portion of the device configured to be handled by a user. The term "distal" refers to portions of the device opposite the proximal side of the device (e.g., portions of the device farthest away from the portions of the device handled by the user). It is also to be understood, however, that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

Cleaning Device and Trocar

FIG. 1 shows a trocar 10 used in minimally invasive surgery. The trocar 10 has a cleaning device 12 removably connected thereto. The cleaning device 12, as shown, is snapped onto the trocar 10 using a snap member 14. However, this is not to be construed as limiting the present disclosure as any suitable attachment element, such as a hook-and-loop fabric, buckles, clips, tape, etc., configured to securely and removably attach the cleaning device 12 to the trocar 10 may be utilized.

An embodiment of cleaning device 12 is depicted in FIG. 1 in an exploded view. The cleaning device 12 comprises a casing 15 having the snap member 14 attached to an outside rear surface thereof. A first depression 24 may be formed in an upper surface of the casing 15 of cleaning device 12 to receive a sponge 20. In one example, the sponge 20 may be impregnated with a cleaning medium 22. The casing 15 may further include a second depression 26 formed in an upper surface thereof and disposed opposite the first depression 24. The second depression 26 may be configured to receive a heating element therein. In one example, the heating element can comprise batteries 16 and a heating coil 18 operatively connected to the batteries 16. The heating coil 18 may be configured to warm a microscope, laparoscope, or other surgical scope (not shown) so that the scope is ready for reinsertion in the trocar 10 and ready for reinsertion into the body of the patient being operated upon. Instead of batteries 16 and heating coil 18, a chemical pack housing chemicals that combine in an exothermic reaction, such as is used by skiers in their gloves to keep their hands warm while skiing, may be used as the heating element.

In one exemplary use of the cleaning device 12, the scope being utilized in a surgical procedure is removed from the trocar 10. It is first wiped off on the sponge 20, thereby to remove matter from the patient which has built up during the surgical procedure or which has condensed upon the scope during the surgical procedure. The heating element is then used to heat the front of the scope, thereby heating the front of the scope above the temperature of the patient to discourage the formation of condensate on the front of the scope when the scope is within the body of the patient. One or more lights 36, such as light emitting diode (LED), may be positioned on casing 15 and used to provide illumination for the trocar 10 and the site where the trocar 10 is inserted into a patient. The lights may be operatively connected to batteries 16.

Figure 2:
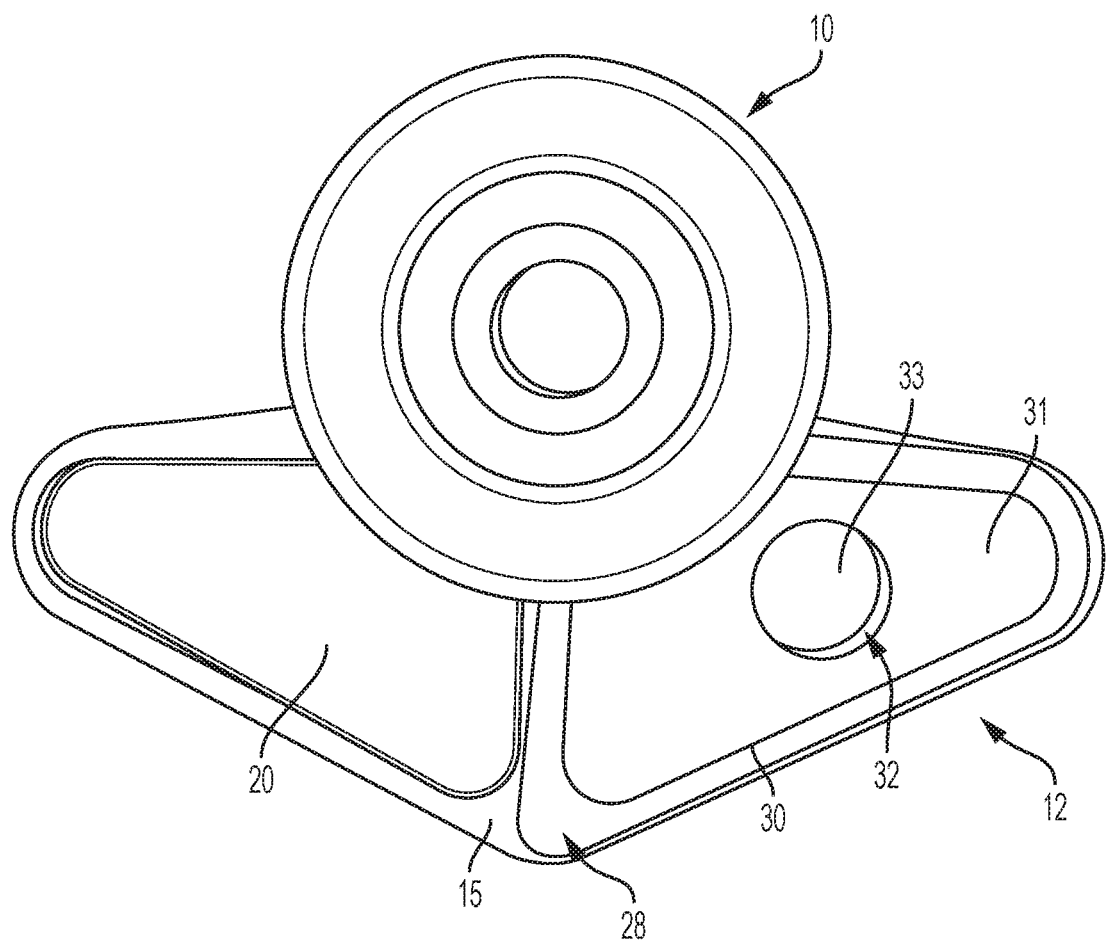
FIG. 2 is a top view of an embodiment of a cleaning device attached to a trocar.

FIG. 2 shows a top view of cleaning device 12 attached to trocar 10. The second depression 26 may further include a heating chamber cover 28 positioned over the top thereof to provide protection for the heating element. The heating chamber cover 28 may further include a microfiber holder 30 formed therein configured to hold a microfiber cover 31. The heating chamber cover 28 and the microfiber cover 31 may be configured with at least one scope access hole 32 which permit the microscope or other scope to be inserted into heating chamber 33 to be warmed by heating coil 18, a heating pack, or some other manner known in the art. Microfiber cover 31 may be used by surgical staff to wipe debris and/or fluids from a scope in order to clean the optics thereof prior to inserting the scope into the scope access hole 32 to be heated. In an embodiment, microfiber cover 31 may be disposed on heating chamber cover 28 within the holder 30 in order to provide easy access to surgical staff.

With further reference to FIG. 2, in one example, casing 15 may have a substantially isosceles triangular shape when viewed from above, with the two sides of the triangle that are not of equal length not adjacent to the trocar 10. Such a configuration may have the benefit of optimizing placement of the heating coil 18 and batteries 16 in casing 15 next to sponge 20. This configuration also may have the benefit of providing easy access to cleaning device 12 while minimizing interference of the device with access to the surgical site while the cleaning device 12 is attached to the trocar 10 during a surgical procedure.

Figure 3:
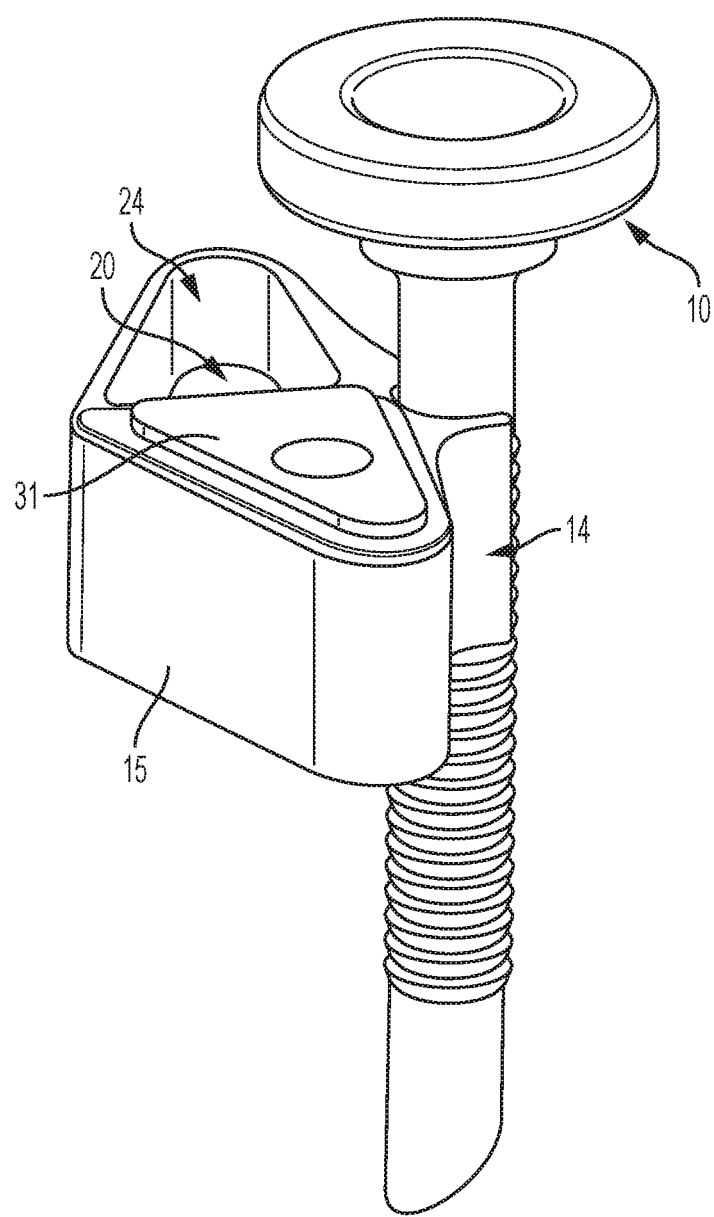
FIG. 3 shows a perspective view of an embodiment of a cleaning device attached to a trocar by a snap member.

In FIG. 3, the trocar 10 is shown again with the cleaning device 12 attached thereto by snap member 14. An advantage of such an embodiment is that it places cleaning device 12 in close proximity to trocar 10, and thereby provides easy access to surgical staff. Such an embodiment also has the advantage that cleaning device 12 does not need to be set on a separate tray.

Figure 4:
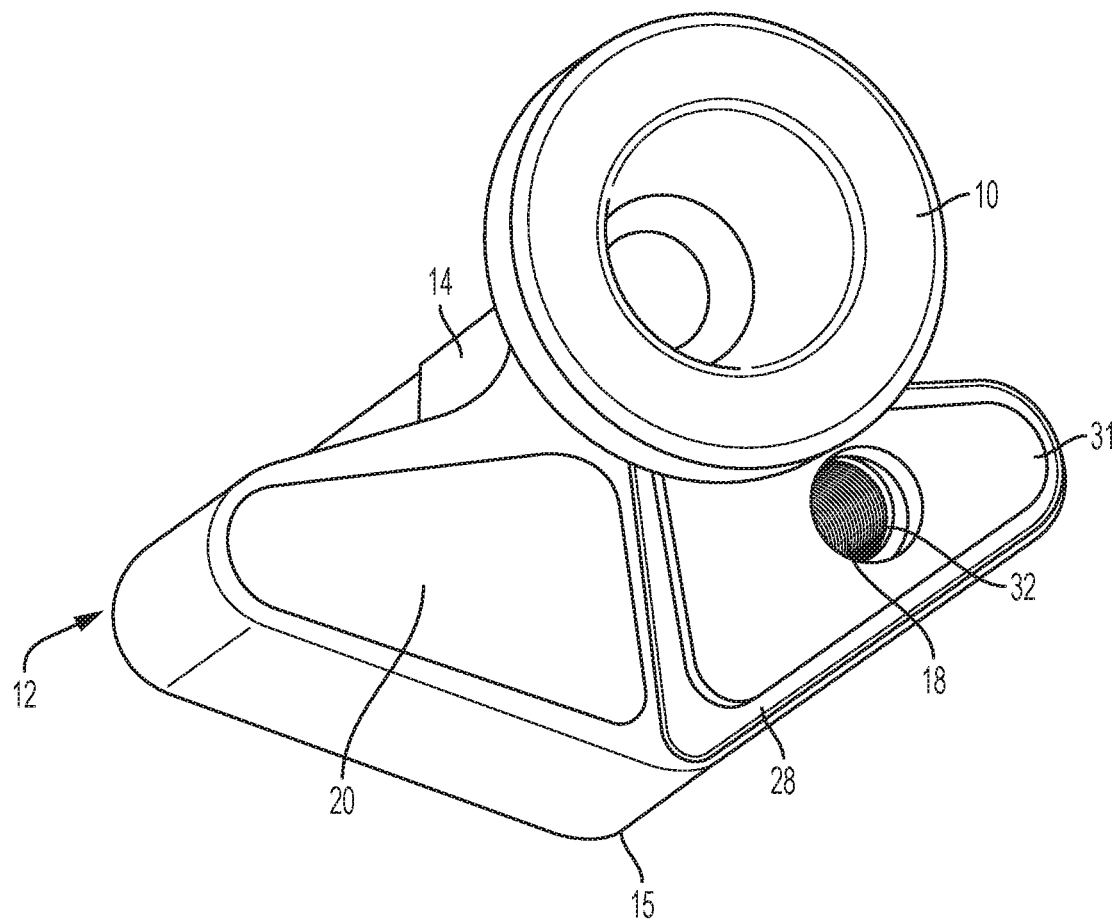
FIG. 4 shows a perspective view of an embodiment of a cleaning device and trocar.

With reference to FIGS. 3 and 4, sponge 20 is shown in its installed position in first depression 24 in casing 15. Sponge 20 may be comprised of any material known in the art. Sponge 20 may be used for cleaning debris and/or fluid from a scope. Sponge 20 also may be impregnated with cleaning medium 22, such as a cleaning and/or defogging fluid. In an embodiment, cleaning medium 22 and/or sponge 20 may be sterile.

FIG. 4 shows the trocar 10 with an embodiment of cleaning device 12 from a different angle than the previous figures. Holes in microfiber cover 31 and heating chamber cover 28 create the scope access hole 32, which allows a scope to access heating chamber 33 in second depression 26, where heating coil 18 may warm and aid in defogging a scope. Debris may be wiped from a scope's optical components by surgical staff on microfiber cover 31 and/or sponge 20, which may be impregnated with cleaning medium 22.

Figure 5:
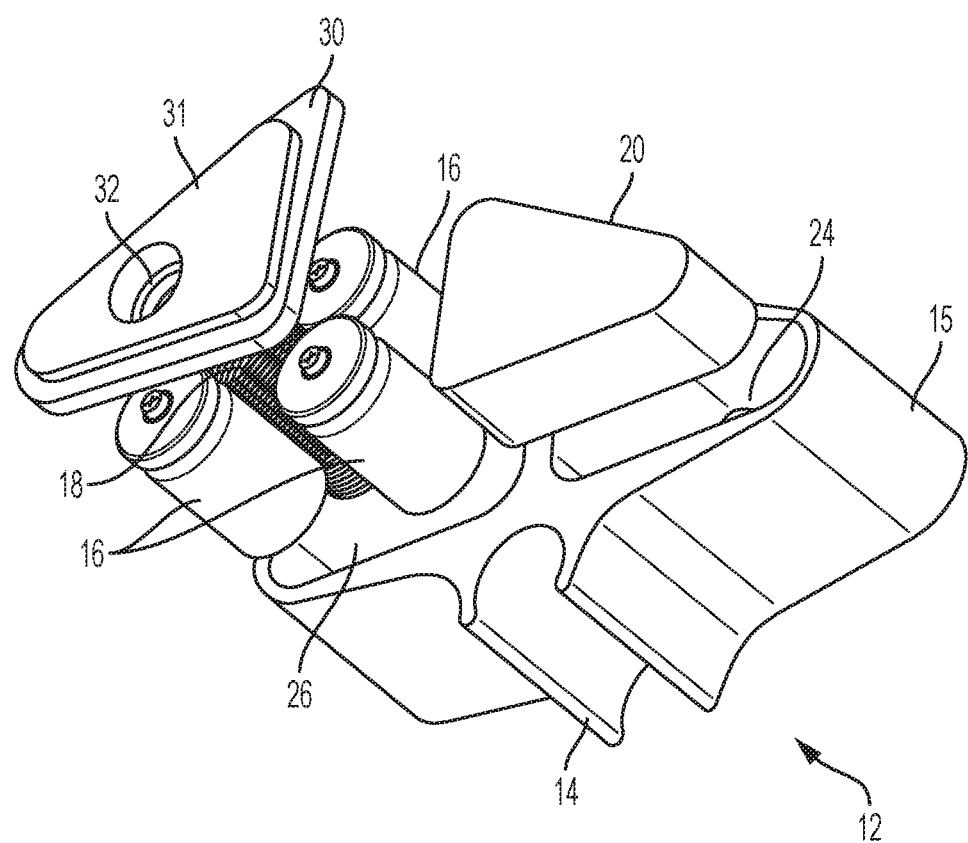
FIG. 5 shows an exploded view of an embodiment of a cleaning device.

FIG. 5 is another exploded view of the cleaning device 12 having the casing 15. The casing 15 comprises an attaching mechanism, such as snap member 14, which is configured to attach to a trocar 10. Snap member 14 is configured to removably attach to trocar 10. Other embodiments of casing 15 may be configured to attach to trocar 10 with tape, a friction fit, or through another mechanism otherwise known in the art.

The casing 15 also comprises a first depression 24, which is configured to hold a sponge 20. The sponge 20 may be at least partially moistened with cleaning medium 22. The casing 15 also comprises second depression 26 which is configured to hold batteries 16 and heating coil 18 or a defogger, and forms heating chamber 33. Second depression 26 may hold one or more batteries 16, which in an embodiment includes three lithium batteries. In other embodiments, other types of batteries 16 may be used or adapted for use, and other numbers of batteries may be used. In another embodiment, another heating source other than an electrical or battery-powered heating source could be utilized, such as a chemical heat source or chemical heat pack, which would avoid the use and ultimate disposal of batteries, which can present challenges due to the potential environmental impact of battery waste.

The second depression 26 and heating chamber 33 of the casing 15 may be at least partially covered by heating chamber cover 28. The heating chamber cover 28 may comprise the microfiber holder 30 and scope access hole 32. A scope or microscope may be inserted into the scope access hole 32 and through the heating coil 18 or defogger. The scope or microscope may be wiped on the microfiber cover 31 disposed in the holder 30 before or after insertion into the scope access hole 32.

In at least one possible embodiment, a structure or material, such as double-sided adhesive tape, could be connected or attached to the casing 15, such as the side or underside, to allow the casing 15 to be connected or attached to a support structure.

Cannula Cleaning Kit

Figure 6:
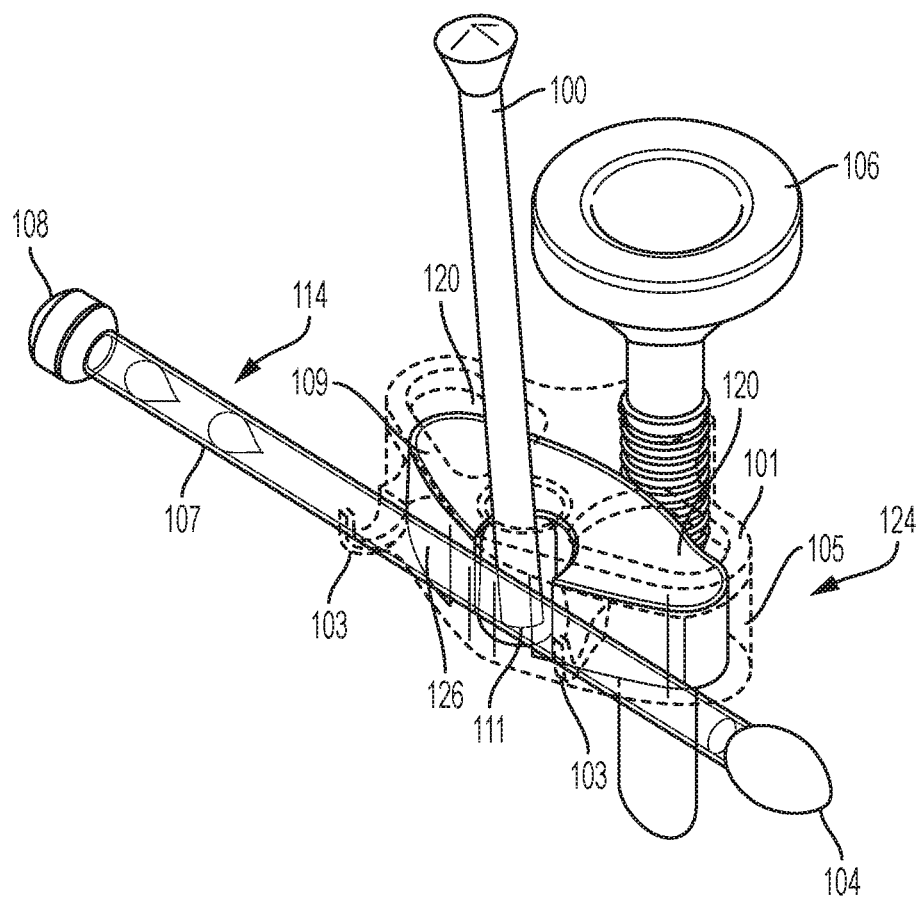
FIG. 6 shows a partially transparent perspective view of an embodiment of a cleaning kit attached to a trocar or cannula.

FIG. 6 shows a partially transparent view of an embodiment of a cleaning kit 124 attached to a trocar 106. The kit 124 includes a container 105 that may house a sponge 110, which may be impregnated with a cleaning solution, and a heater 109. A cover 101 is located on top of the container 105. The cover 101 has an opening therein into which can be inserted a surgical viewing device 100, such as a scope, laparoscope, or microscope, such that the scope lens 111 is inside the container 105. In an embodiment, cover 101 may include one or more recesses 120, at least one of which contains a microfiber wipe or cleaner 102. Also shown is a cannula cleaner 114, which is held by two cannula cleaner tube holders 103. Holders 103 may removably secure the cannula cleaner 114 to the container 105 when it is not in use during a surgical procedure. Cannula cleaner 114 may be secured by a friction fit, or in some other manner otherwise known in the art. In addition, the cover 101 may have one or more projections 126 that project out above the cannula cleaner 114 to further secure the cannula cleaner 114 in place in a secured position on container 105.

An embodiment of cannula cleaner 114 may include an elongated body with a cleaning tip 104 disposed at one end. In an embodiment, the body of the cannula cleaner 114 may comprise a tube that also functions as a solution container 107. On the end opposite the cleaning tip 104 is located a solution dispensing valve 108. Either the valve 108 or the solution container 107 may be squeezed, pinched, or pressed in to cause an amount of a cleaning or defogging solution, or some other liquid known in the art, to be dispensed. The solution may be dispensed into the container 105. By containing the solution in the cannula cleaner 114, a supply of cleaning solution is readily available to be dispensed into the container 105, and is in easy reach for a user of the trocar 106 and cleaning kit 124, such as by a surgeon or other medical professional. By mounting the cannula cleaner 114 on the container 105, the cannula cleaner 114 is easy to reach for use in cleaning or clearing out the trocar 106. The design of the cannula cleaner 114, therefore, combines a cleaning device with a cleaning solution supply, so as to facilitate keeping the trocar 106 and viewing instruments clean during a surgical procedure. However, it should be understood that other embodiments of cannula cleaner 114 may exist, such as an embodiment that does not hold solution and lacks a solution dispensing valve 108. Another embodiment may include cleaning tips 104 at both ends of the cleaning device 114. In such an embodiment, the cleaning tips 104 may be of the same size or of different sizes. Cannula cleaning tip 104 may be comprised of a sponge, foam, microfiber, or some material otherwise known in the art.

Figure 7:
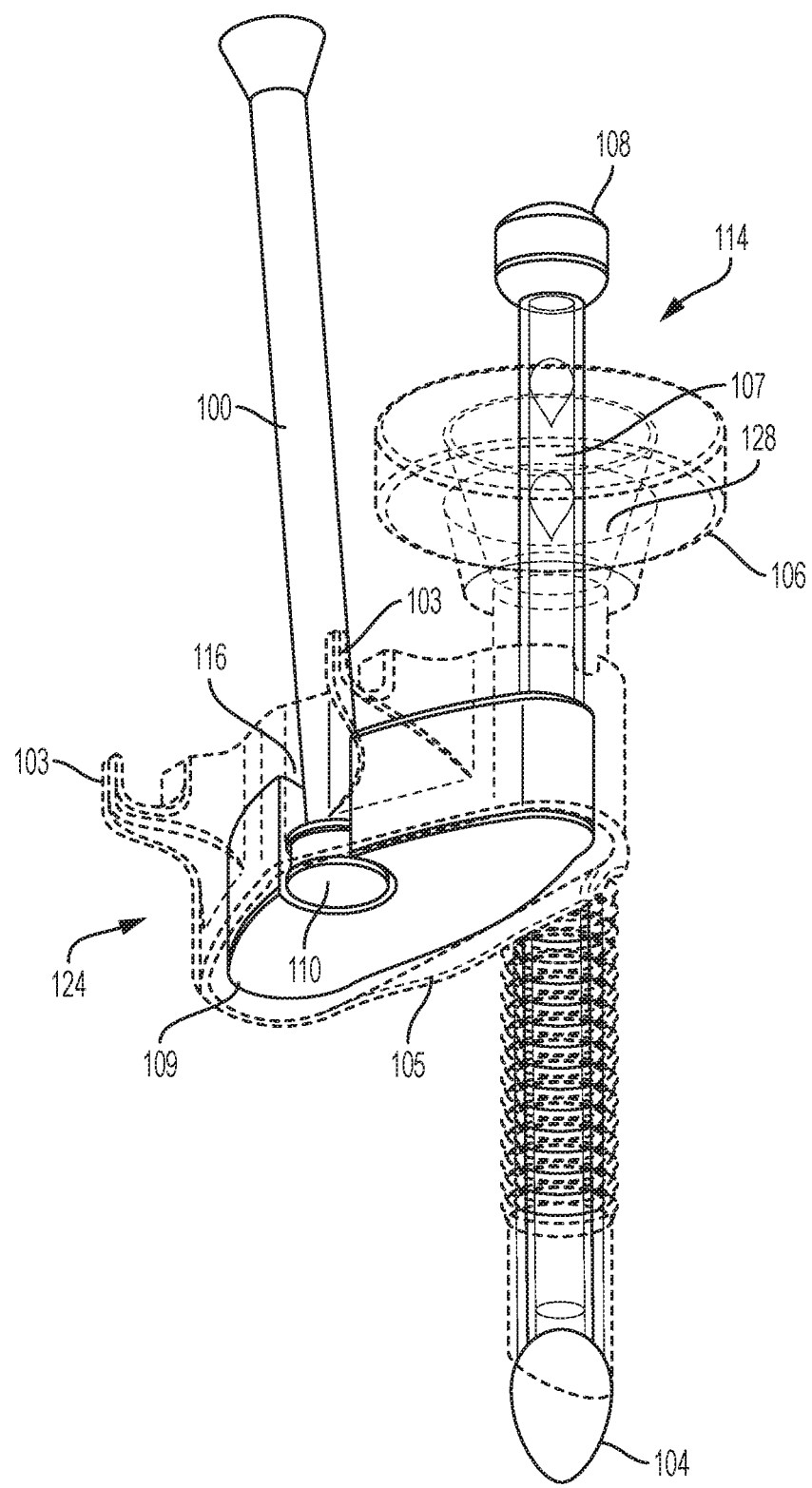
FIG. 7 shows another view of an embodiment of the cleaning kit shown in FIG. 6.

FIG. 7 shows another view of the cleaning kit 124 shown in FIG. 6. In FIG. 7, container 105 is shown as transparent in order to demonstrate how scope 100 may be inserted through scope access hole 116, so that the optics thereof may contact sponge 110. However, it should be understood that not all embodiments of container 105 need be transparent. FIG. 7 also depicts how scope 100 may interact with an embodiment of heater 109. In an embodiment, heater 109 may be configured to surround or partially surround scope 100, and may substantially border the perimeter or part of the perimeter of sponge 110. Heater 109 and sponge 110 may be configured to create a substantially cylindrical space, where the lens 111 of a scope 100 may be inserted for cleaning and/or defogging, which may be preferable to engage embodiments of scopes 100 that are substantially cylindrically-shaped. In an embodiment, sponge 110 may be configured to maximize efficient contact with lens 111 of scope 100. In an embodiment, sponge 110 may be substantially circular in shape. Embodiments of heater 109 may comprise other shapes. Embodiments of heater 109 may use electrical or chemical processes to generate heat, or may do so using another manner known in the art.

With further reference to FIG. 7, cannula cleaner 114 may be inserted into a cannula 128 of trocar 106 to clean the cannula 128 of fluids, condensates, and/or debris. In an embodiment, cannula cleaning tip 104 may be inserted into cannula 128. In an embodiment, cannula cleaning tip 104 may have a diameter that is substantially the same or larger than the diameter of the cannula 128. Cannula cleaning tip 104 may be comprised of a deformable material, and deform to fit into cannula 128 while contacting the walls of the cannula 128. Cannula cleaning tip 104 may be sufficiently absorptive to absorb fluids and/or condensate present in trocar 106. Trocar 106 is shown as transparent in order to better illustrate the insertion of cannula cleaner 114 therein; however, it should be understood that embodiments of trocar 106 need not be transparent.

Figure 8:
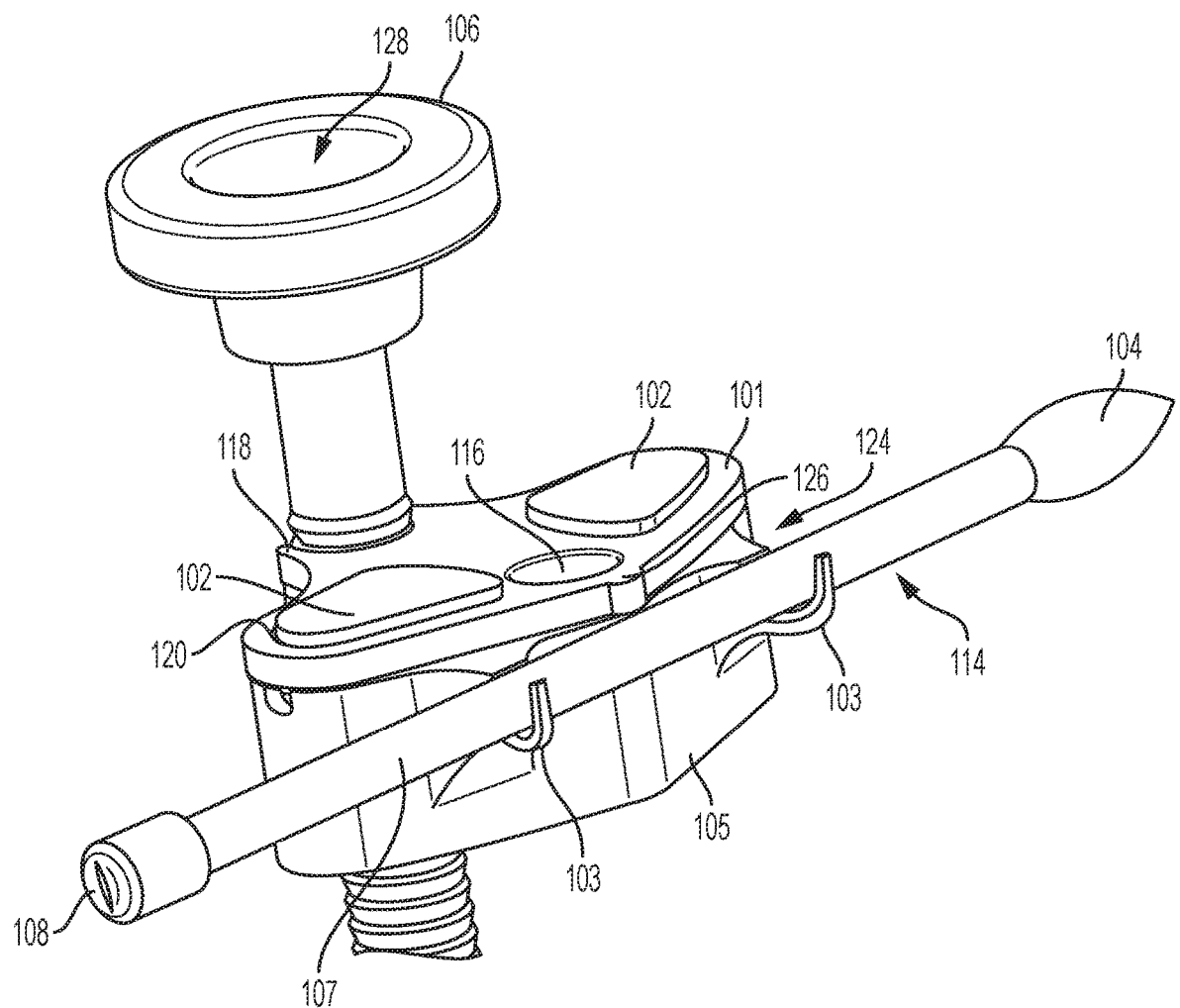
FIG. 8 shows another view of an embodiment of the cleaning kit shown in FIG. 6.

FIG. 8 shows a perspective view of the cleaning kit 124 depicted in FIG. 6. Cannula cleaner 114 is shown disposed on cannula holders 103, which are configured to contain cannula cleaning device 114 against container 105 during a surgical procedure when cannula cleaner 114 is not in use. In an embodiment, cover 101 of cleaning kit 124 may include projection 126 that is configured to further constrain cannula cleaner 114 when not in use. Cover 101 may include one or more microfiber wipes 102 disposed thereon to further aid in cleaning debris or condensate from a scope 100. While the embodiment shown in FIG. 8 shows a configuration wherein two microfiber wipes 102 are positioned on cover 101 roughly on either side of scope access hole 116, it should be understood that other configurations or numbers of wipes 102 may be used. It also should be understood that embodiments of cover 101 need not include microfiber wipes 102, and that other materials or wiping elements otherwise known in the art may be used to wipe debris from the lens 111 of a scope 100. Wipes 102 may be disposed in one or more recesses 120 in cover 101. Cleaning kit 124 may removably attach to trocar 106 by a snap member 118, or another manner known in the art.

Figure 9:
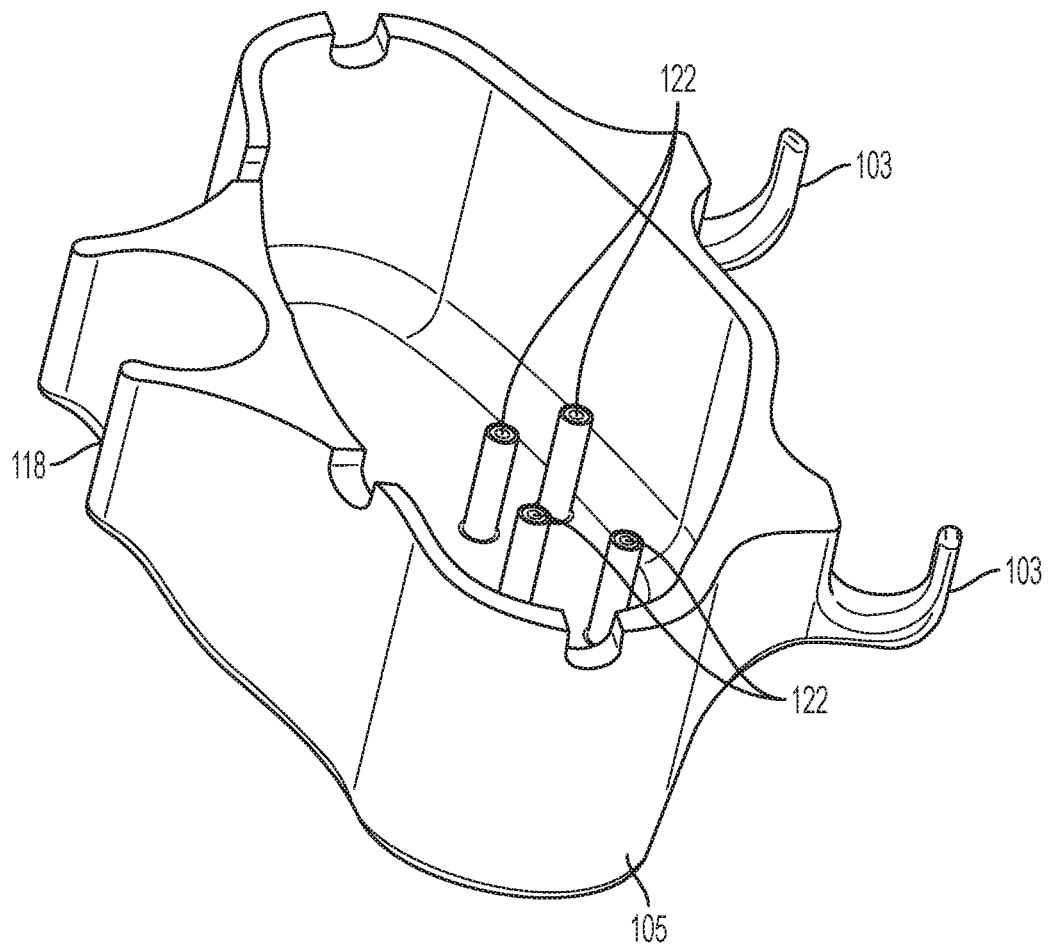
FIG. 9 shows a view of a container of an embodiment of the cleaning kit shown in FIG. 6.

FIG. 9 shows a perspective view of a portion of the container 105 of the cleaning kit 124 shown in FIG. 6. An embodiment of container 105 may be integrally molded with snap member 118 and/or one or more cannula cleaning device holder 103. The interior of container 105 may comprise a single chamber, or multiple chambers. The at least one chamber may include one or more support posts 122. Support posts 122 may provide support for cover 101, and may provide support for configurations of heater 109. In embodiments of heater 109, posts 122 may support configurations of batteries, a heating coil chemical packs, or other components of a heater 109 otherwise known in the art.

Figure 10:
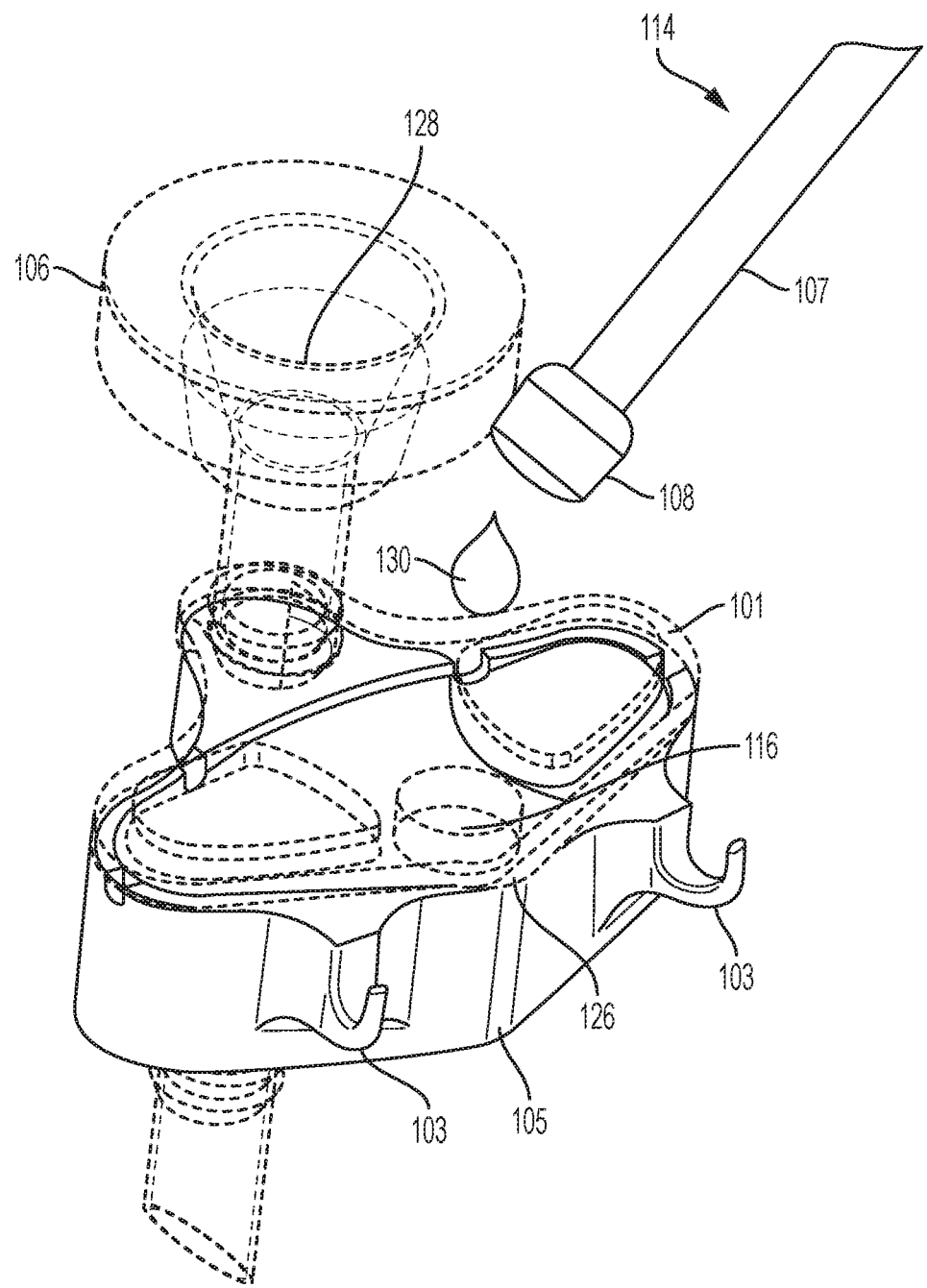
FIG. 10 shows another view of the embodiment of the cleaning kit shown in FIG. 6, with a cannula cleaner being used to dispense a cleaning medium.

FIG. 10 shows another view of the cleaning kit 124. In an embodiment, cannula cleaner 114 may be used to dispense cleaning and/or defogging solution into container 105 through scope access hole 116. In an embodiment, solution may exit solution container 107 of cannula cleaner 114 through solution dispensing valve 108. When solution—represented by a droplet of cleaning solution 130—enters through scope access hole 116, it may contact and be absorbed by sponge 110. A scope may then be inserted into container 105 through scope access hole 116 and contact impregnated sponge 110, which may aid in cleaning and/or defogging the scope 100.

Figure 11:
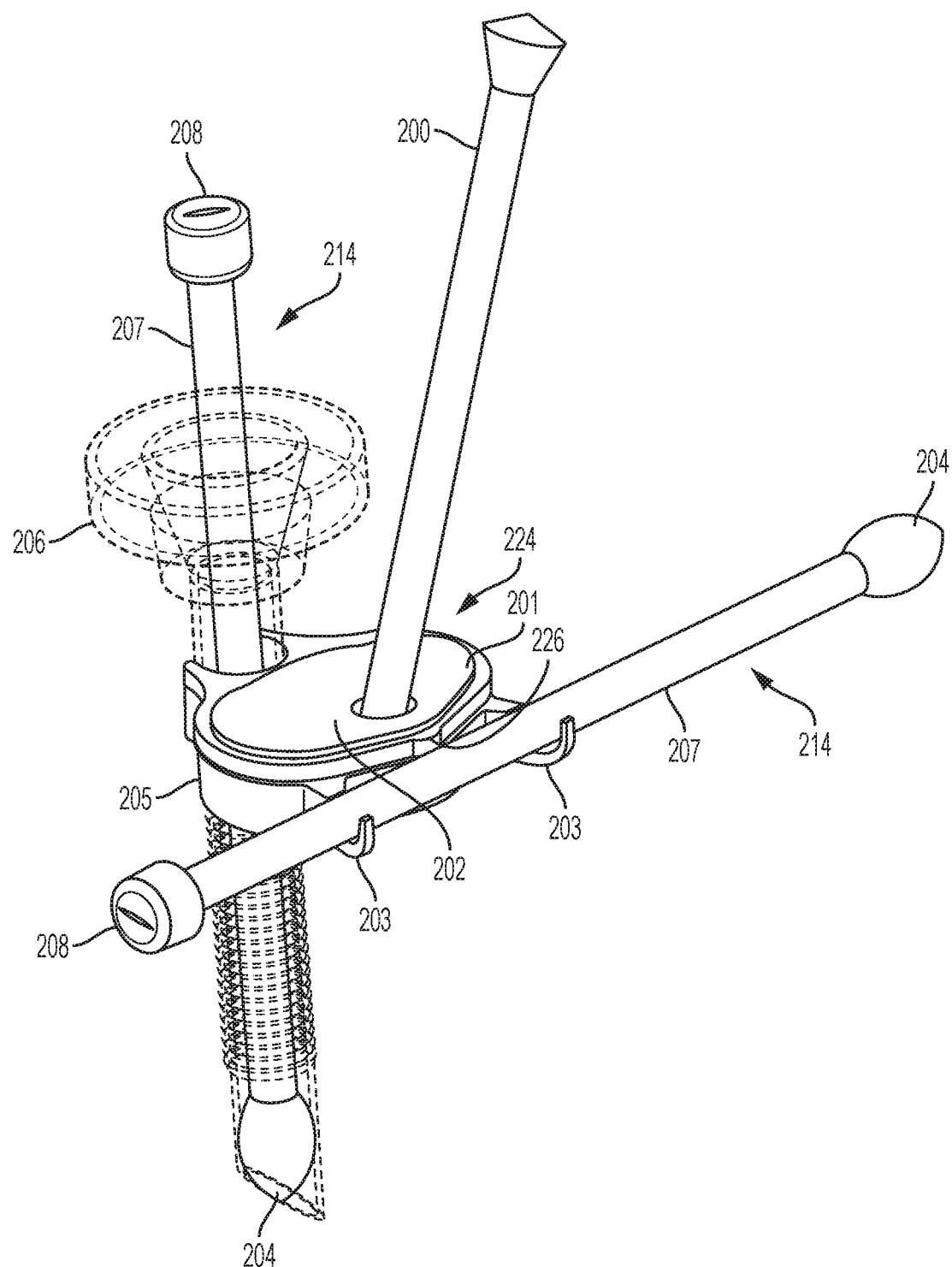
FIG. 11 shows an embodiment of a cleaning kit.
Figure 12:
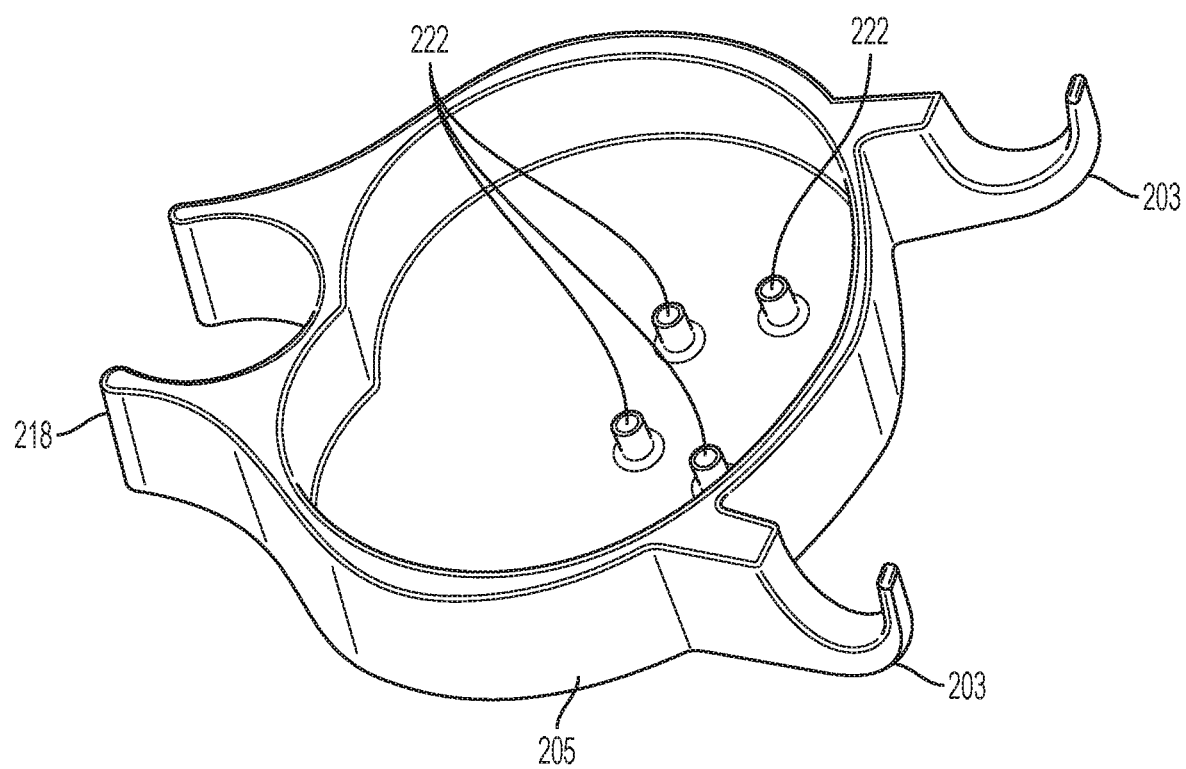
FIG. 12 shows a view of a container of an embodiment of the cleaning kit shown in FIG. 11.

With reference to FIGS. 11 and 12, an alternative embodiment of a cleaning kit 224 is illustrated. Cleaning kit 224 is configured to clean lens 211 of a scope 200 and may include a container 205 that is shorter or thinner than the embodiment of the container 105 shown in FIG. 6. In the example in FIG. 11, no batteries are utilized, so a shorter or thinner container 205 can be utilized. In an embodiment, the kit may use no heating device or heating medium. In another embodiment, a chemical heating medium or chemical heating pack may be used which takes up less space than batteries. Cover 201 also may include a microfiber wipe or cleaner 202 that spans most or all of the surface area of cover 201. FIG. 11 depicts two cannula cleaners 214 in order to demonstrate both insertion into trocar 206, and placement in cleaner tube holders 203. However, it should be understood that not all embodiments of cleaning kit 224 require more than one cannula cleaner 214. Each of the cannula cleaners may include a cannula cleaning tip 204 at a first end thereof, a solution container 207 extending between the first end and second end thereof, and a solution dispensing valve 208 positioned at the second end.

FIG. 12 shows a view of container 205 of the embodiment of the cleaning kit 224 shown in FIG. 11. In an embodiment, snap member 218 and one or more cannula cleaner holders 203 may be integrally molded with container 205. The container 205 may comprise a chamber, and may include one or more internal supports 222. In one example, internal supports 222 may be used to support cover 201, or constrain a heater and/or sponge.

Cleaning Device with Snap Fit Connector

With reference to FIGS. 13-19, another embodiment of cleaning device 310 configured for cleaning a surgical tool, such as a surgical scope, prior to insertion of the tool into a body of a patient during minimally invasive surgery, is illustrated. As described herein, the cleaning device 310 includes a connector 312, such as a snap fit connector, which is configured to removably mount the cleaning device 310 to tubular or cylindrical objects having different maximum outer diameters without needing to adjust or reposition the connector 312 to accept and engage the different sized structures. As used herein, the cleaning device 310 is described as being connected to trocars used in surgical procedures. However, it is understood that the connector 312 can also be used for mounting the cleaning device 310 to other tubular bodies and structures including, for example, rods, posts, railings, pieces of furniture, as well as other medical devices and tools located at a surgical scene.

Figure 18:
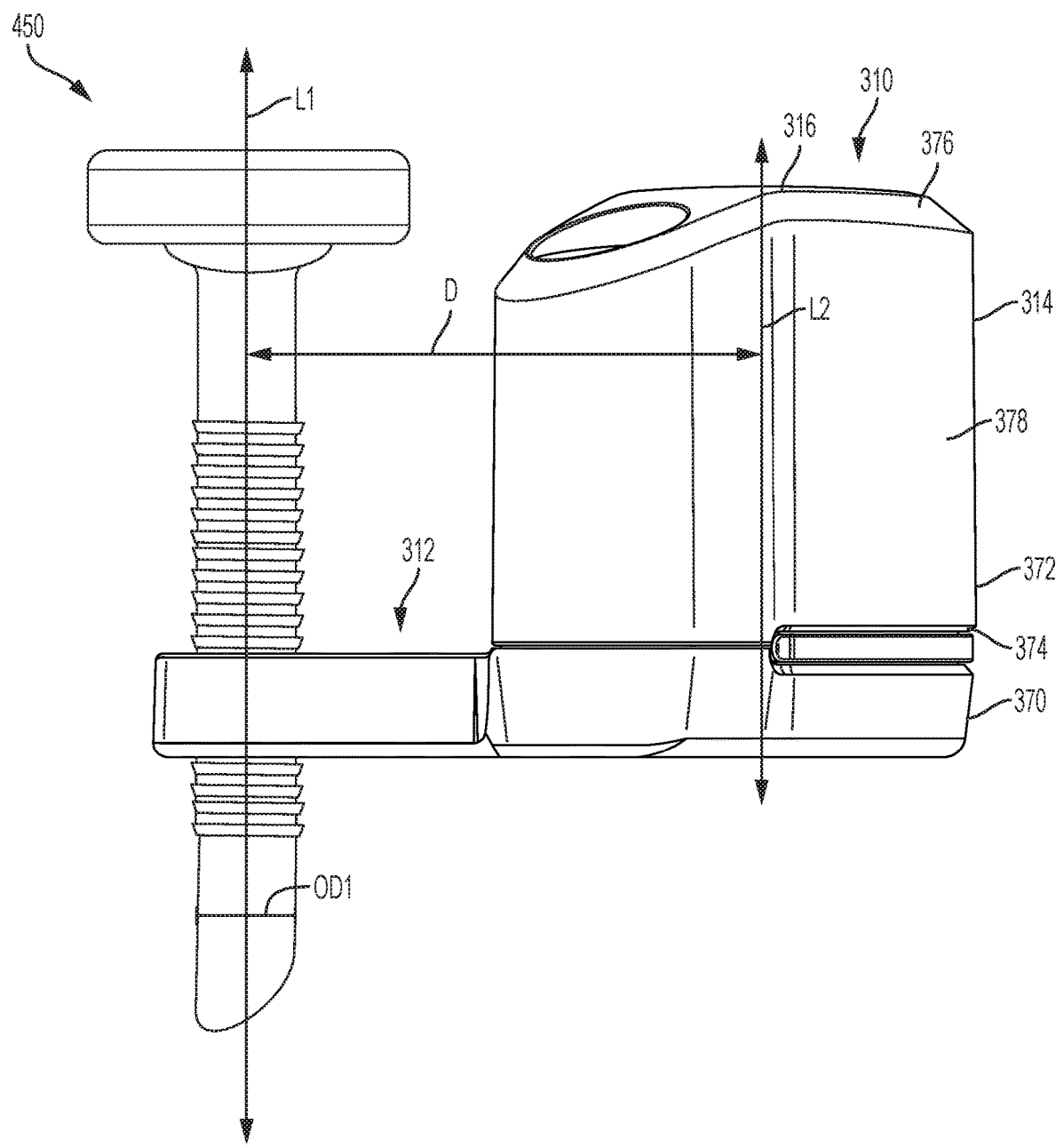
FIG. 18 is a side view of the surgical tool cleaning device of FIG. 13 connected to a trocar having a first diameter.
Figure 19:
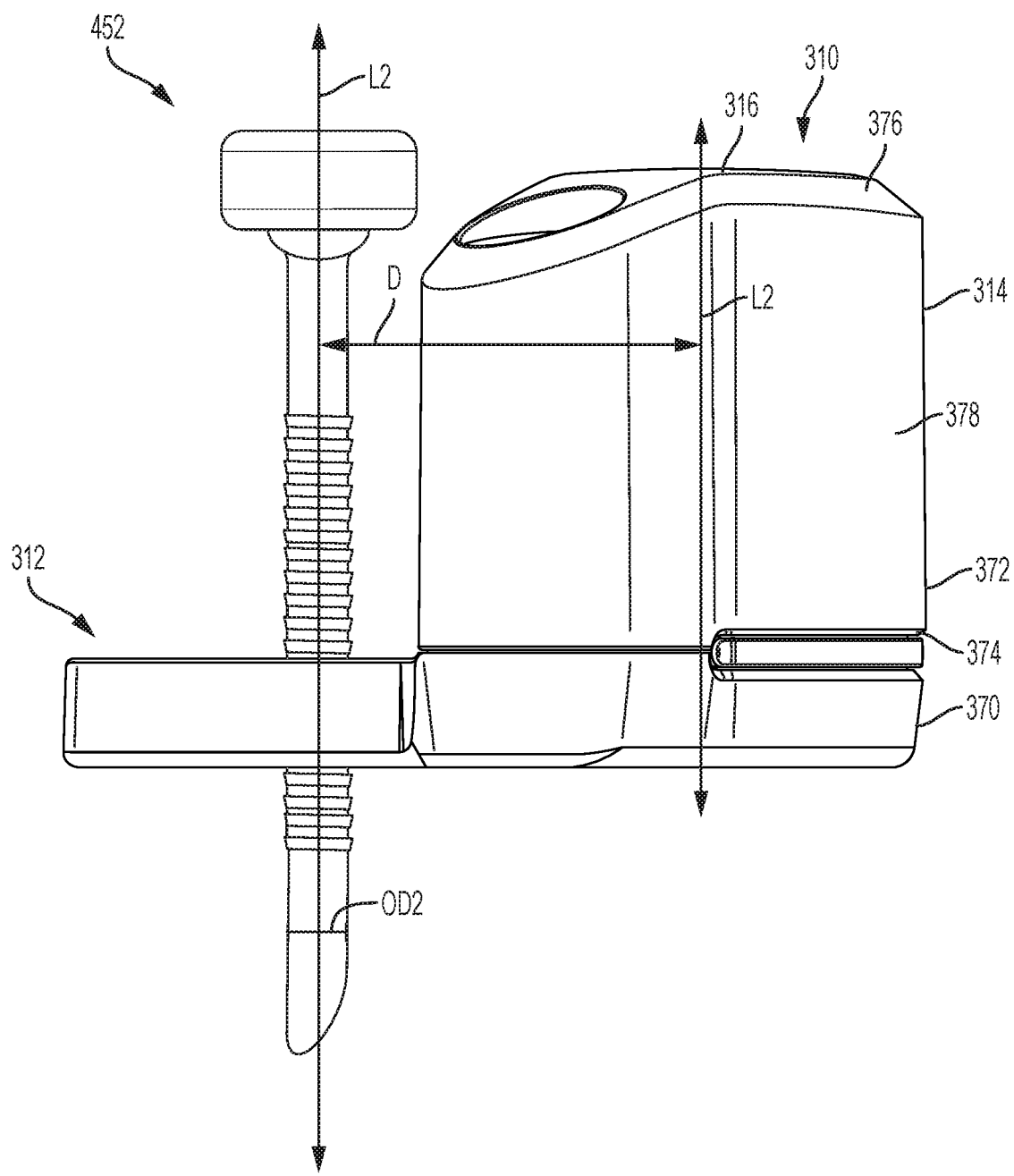
FIG. 19 is a side view of the surgical tool cleaning device of FIG. 13 connected to a trocar having a second diameter.
Figure 20:
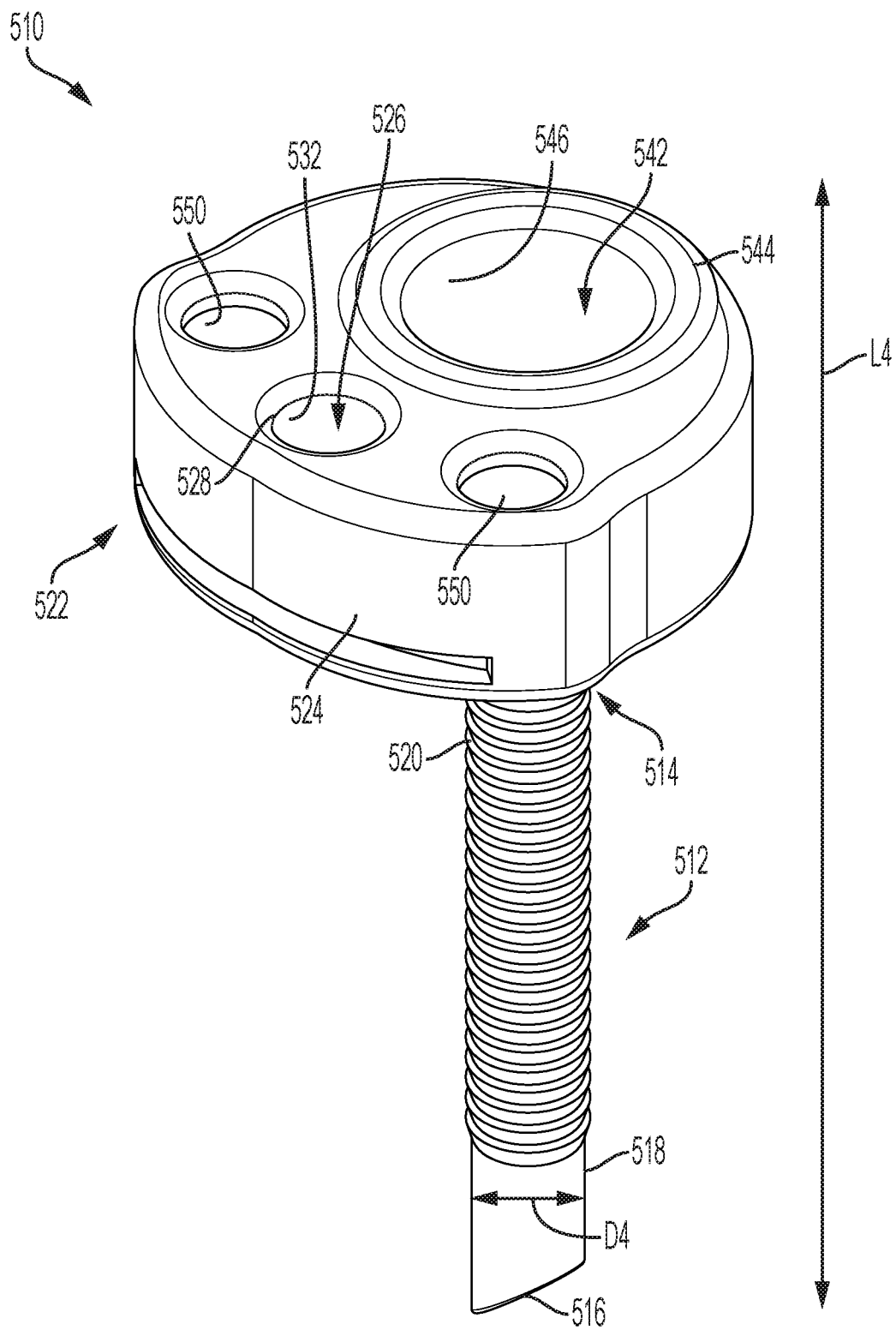
FIG. 20 is a perspective view of another embodiment of a surgical tool cleaning device and trocar, according to an aspect of the disclosure.

In some examples, the connector 312 can be configured to removably attach the cleaning device 310 to two different standard sized surgical trocars 450, 452 (shown in FIGS. 18 and 19). For example, the connector 312 can be configured to receive a large diameter trocar 450 (shown in FIG. 18), such as a trocar having a maximum outer diameter OD1 of from 6.0 mm to 18.0 mm, preferably having a maximum outer diameter of about 8.0 mm. The connector 312 can also be configured to receive a smaller diameter trocar 452 (shown in FIG. 19), such as trocar having an outer maximum diameter OD2 of from 1.0 mm to 6.0 mm, preferably about 4.0 mm. The connector 312 is configured to connect to one trocar at a time (either the single small (e.g., 4.0 mm) diameter trocar or the single large diameter (e.g., 8.0 mm) trocar). While the connector 312 may connect to other similar sized trocars (e.g., trocars having a maximum outer diameter within 5% or 10% of the designated size), the connector 312 is not designed to connect to a wide range of different trocar sizes. For example, the connector 312 is not designed to be adjusted or reconfigured for use with a range of trocar diameters. Desirably, portions of the connector 312 are naturally biased or sized to frictionally engage the trocar to hold the connector 312 and cleaning device 310 in place relative to the trocars 450, 452. Therefore, as described herein, the user does not need to, for example, tighten the connector 312 to secure the connector 312 to the trocar, cinch down a portion of the connector against the trocar, or perform some other action for adjusting the connector 312 to receive different sized trocars. Instead, the user need only insert the tubular portion of the trocar of either size (e.g., either 4.0 mm trocar or the 8.0 mm trocar) into the connector 312 to removably attach the cleaning device 312 to the trocar.

In some examples, the cleaning device 310 includes a protective outer structure such as a housing 314, casing, or other enclosure having at least one opening 316 for accessing an interior 318 of the housing 314. The housing 314 can be formed from any suitable rigid and substantially fluid tight material, such as plastic, rubber, ceramics, glass, or metal. Desirably, the housing 314 is lightweight and can be supported by a surgical tool, such as the trocar, without damaging the housing 314 or cleaning device 310. Accordingly, such housings are often formed from rigid lightweight plastics (e.g., polyesters, copolyesters, polyethylene terephthalate (PET), polystyrene, high-density polyethylene, polycarbonate, or similar materials).

As in previous embodiments, the cleaning device 310 also includes a sponge 320 (shown in FIG. 15) immersed in a defogging solution and a heater assembly 322 (shown in FIG. 15) in an interior 318 of the housing 314. For example, the sponge 320 can be a circular or cylindrical sponge having an outer diameter OD3 (shown in FIG. 15) of from about 15 mm to about 25 mm. The housing 314 and housing interior 318 are generally sized to receive a lens of a surgical tool, such as a laparoscope, endoscope, or cytoscope. Accordingly, dimensions of the housing 314 and interior 318 are selected so that the lens of the scope can be easily inserted into the interior 318 through the opening 316 to contact the sponge 320 and/or to be brought into proximity to the heater assembly 322. For example, the housing 314 can be from about 40 mm to 60 mm in height H1 and about 50 mm to about 70 mm in width W1.

The cleaning device 310 further includes the connector 312, which is configured to removably attach the housing 314 to the trocar, thereby supporting the housing 314 relative to the trocar. For example, the connector 312 can be configured to support the housing 314, such that a central longitudinal axis L1 (shown in FIGS. 18 and 19) of a portion of the trocar 450, 452 received by the connector 312 is spaced apart from the interior 318 of the housing 314. Similarly, the connector 312 can be configured to support the housing 314, such that a line L2 (shown in FIGS. 18 and 19) normal to a bottom surface and passing through the opening 316 of the housing 314 is parallel to and a fixed distance D1 (shown in FIGS. 18 and 19) from the central longitudinal axis L1 of the trocar 450, 452.

With specific reference to FIGS. 13-17, features of an exemplary connector 312 configured to receive the different sized trocars will now be discussed in detail. The connector 312 can include a first arm 324 and a second arm 326 extending from an outer surface 328 of the housing. The arms 324, 326 can be integrally formed with other portions of the housing 314. For example, the housing 314 and arms 324, 326 can be formed together by a suitable plastic molding process, such as injection molding. In other examples, the arms 324, 326 can be formed separately from other portions of the housing 314 and mounted to the outer surface 328 of the housing 314 by a suitable adhesive, fastener, or combination thereof. As described herein, the arms 324, 326 are sized to receive the different sized trocars and to hold the cleaning device 310 in a fixed position relative to the trocar. In order to receive the trocar, an inner surface 330 of the first arm 324 and an inner surface 332 of the second arm 326 may define at least a first recess 334, shown by circle C1 in FIGS. 16 and 17, sized to receive a trocar having a first diameter. The arms 324, 326 may also define at least one second recess 336, shown by circle C2 in FIGS. 16 and 17, sized to receive a trocar having a smaller diameter.

In order to permit mounting the cleaning device 310 to the trocar, the first arm 324 and the second arm 326 of the connector 312 can be configured to deflect radially outwardly, in a direction of arrow A1 (shown in FIGS. 16 and 17) from the first recess 334 and/or the second recess 336 to receive the trocar. The arms 324, 326 are also configured to move radially inwardly, in a direction of arrow A2 (shown in FIGS. 16 and 17) to engage the trocar.

In some examples, the first arm 324 and the second arm 326 include a first end 338, 340 mounted to a portion of the outer surface 328 of the housing 314 and a free second end opposite the first end 338, 340. In order to secure the trocar within the recess 334, 336, the arms 324, 326 can include a protrusion 342, 344 positioned at the free end of each arm 324, 326. The protrusions 342, 344 can include an inwardly angled outer surface 346 configured to direct the trocar into the first recess 334 and/or into the second recess 336. The protrusions 342, 344 can also include an inner surface 348 configured to engage the trocar to retain the trocar within the first recess 334. For example, the inner surface 348 can have a curvature which matches the curvature of the trocar.

The trocar enters the first recess 334 through a space 350 between the opposing protrusion 342 of the first arm 324 and the protrusion 344 of the second arm 326. For example, the user may press the trocar in a direction of arrow A3 through the space 350 and into the first recess 334. If the trocar is small enough (e.g., has a maximum outer diameter of less than about 6.0 mm) to pass from the first recess 334 into the second recess 336, the user can advance the trocar in a direction of arrow A4 into the second recess 336 through a second space 352 between portions of the first arm 324 and the second arm 326.

In some examples, the recesses 334, 336 are formed by curved portions or regions of the first arm 324 and the second arm 326. For example, the inner surface 330 of the first arm 324 and the inner surface 332 of the second arm 326 may each include a first curved portion 354 having a first radius R1 sized such that the first curved portion 354 engages a trocar of the first diameter OD1 (shown in FIG. 18). The arms 324, 326 can also include a second curved portion 356 having a radius R2, sized such that the second curved portion 356 engages a trocar with the second diameter OD2 (shown in FIG. 19).

In some examples, portions of the first arm 324 and/or the second arm 326 configured to contact the trocar can include textured or high friction surfaces 358 configured to enhance the frictional engagement between the trocar and the inner surface 330, 332 of the first arm 324 and/or the second arm 326. For example, the textured surface 358 can include a plurality of longitudinally extending ribs 360 extending radially inwardly from inner surfaces 330, 332 of the first arm 324 and/or the second arm 326.

In some examples, the connector 312 can also include a third recess 362 (shown by the circle C3 in FIGS. 16 and 17) for connecting the device 310 to a trocar of a third diameter, which is smaller than the first diameter or the second diameter. For example, the third recess 362 can be sized to receive a trocar with a maximum outer diameter of about 2.0 mm or less. The third recess 362 can be accessible through a space 364 between the portions of the arms 324, 326 that form the second recess 336.

Figure 13:
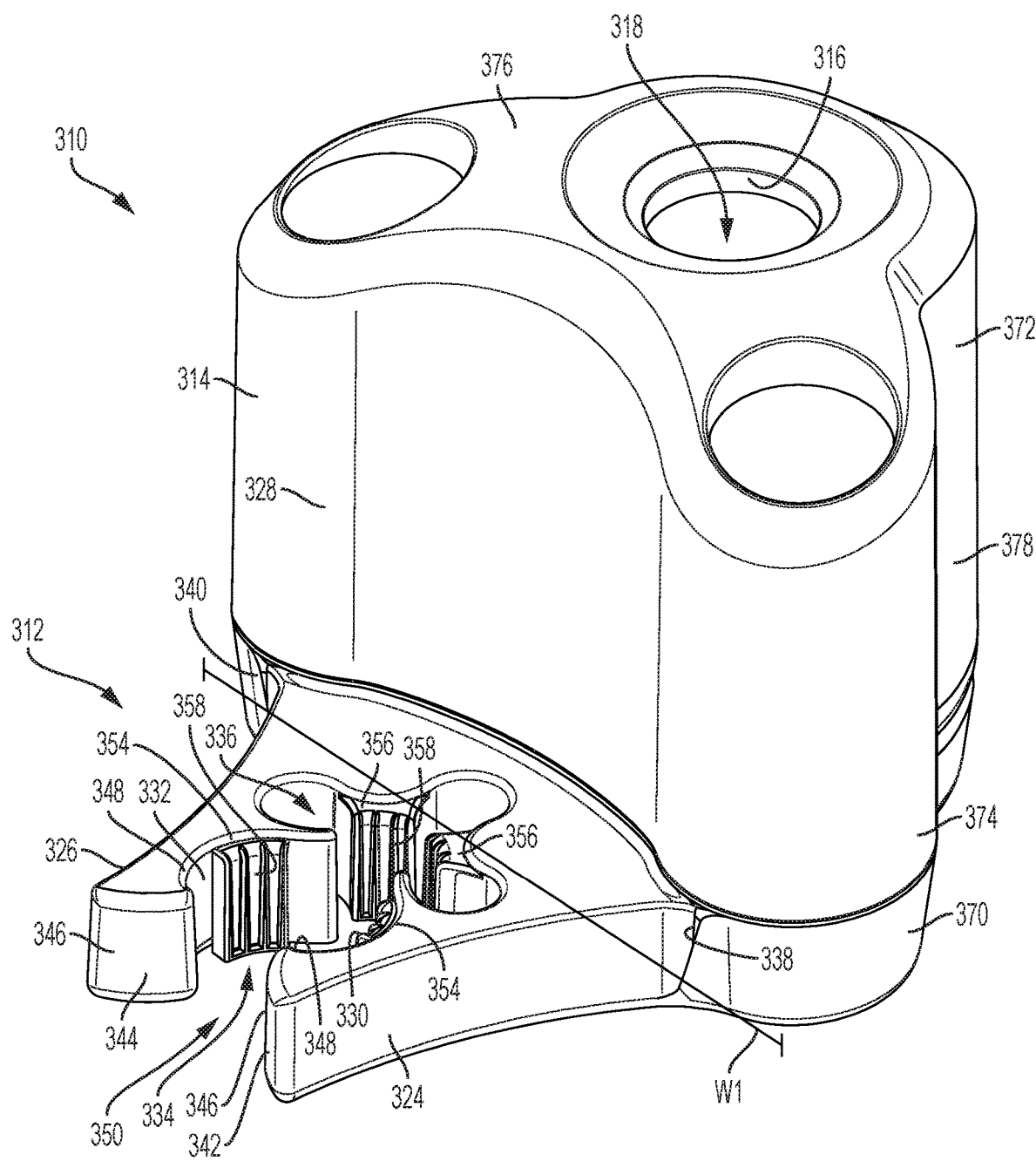
FIG. 13 is a perspective view of another embodiment of a surgical tool cleaning device according to an aspect of the present disclosure.
Figure 14:
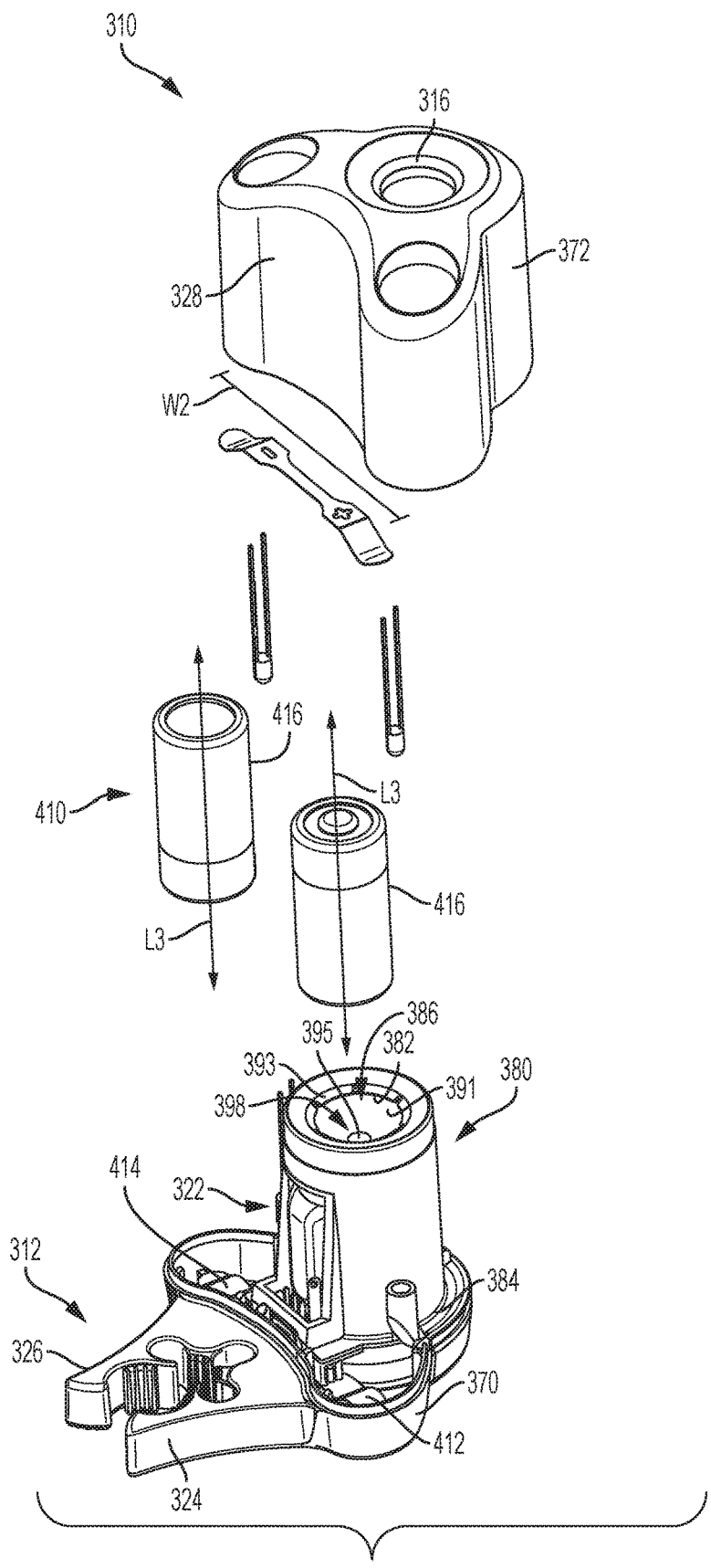
FIG. 14 is an exploded perspective view of the surgical tool cleaning device of FIG. 13.

With reference again to FIGS. 13-15, in some examples, the housing 314 is formed from multiple individually formed or molded pieces joined together to form an enclosure. For example, the housing 314 can include a base 370 integrally formed with the connector 312. The housing 314 can also include a cover 372, such as a dome shaped cover, having an open bottom portion 374, a partially closed top portion 376, and an annular sidewall 378 extending therebetween. As shown in FIGS. 13 and 14, the at least one opening 316 for accessing the interior 318 of the housing 314 can be positioned on the top portion 376 of the cover 372. As described herein, additional structures formed from other materials can be attached to the base 370 and/or connector 312 using a suitable adhesive or molding process. For example, as described herein, the textured or high friction surface 358 of the connector 312 can be formed by overmolding a textured or high friction material to the connector 312 to enhance the frictional engagement between the connector 312 and trocar.

Figure 15:
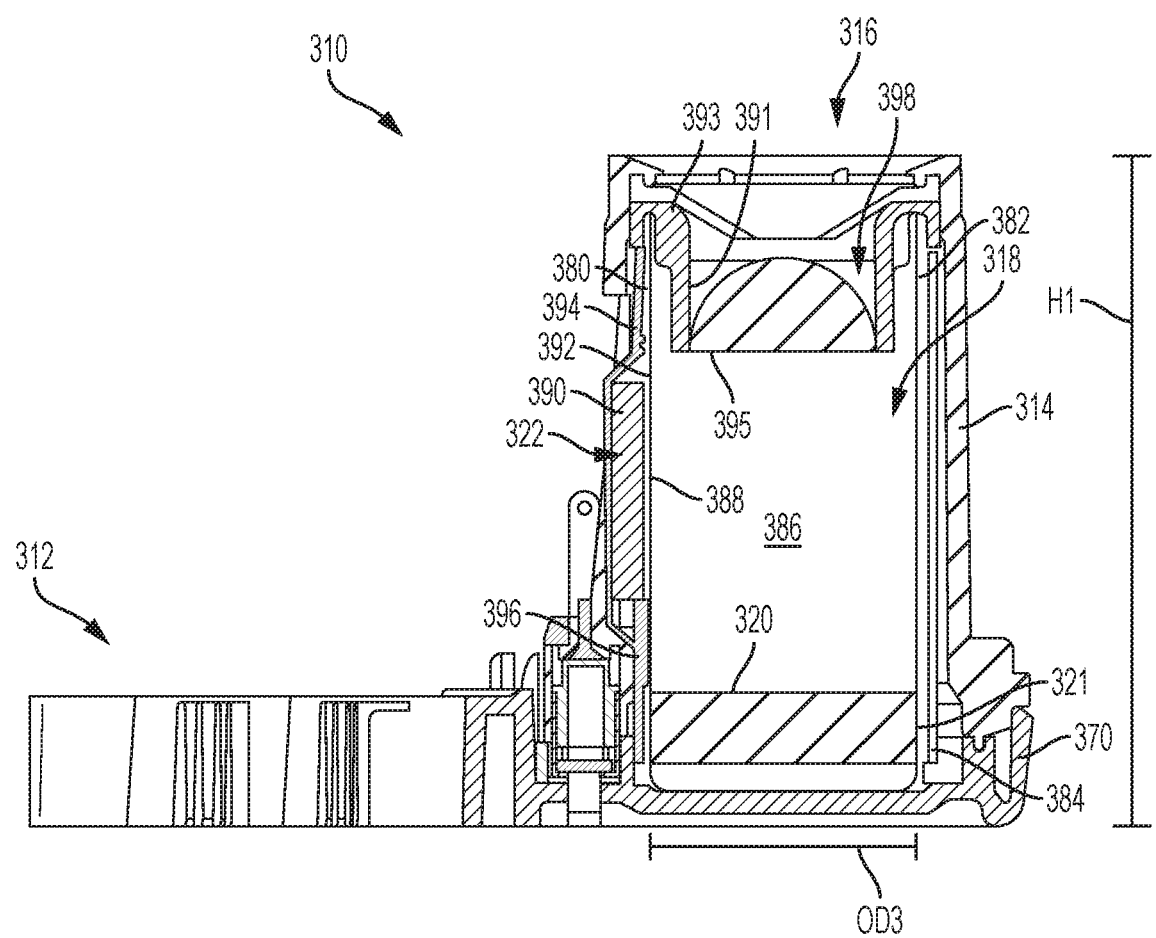
FIG. 15 is a cross-sectional view of the base and the fluid reservoir of the surgical tool cleaning device of FIG. 13.
Figure 16:
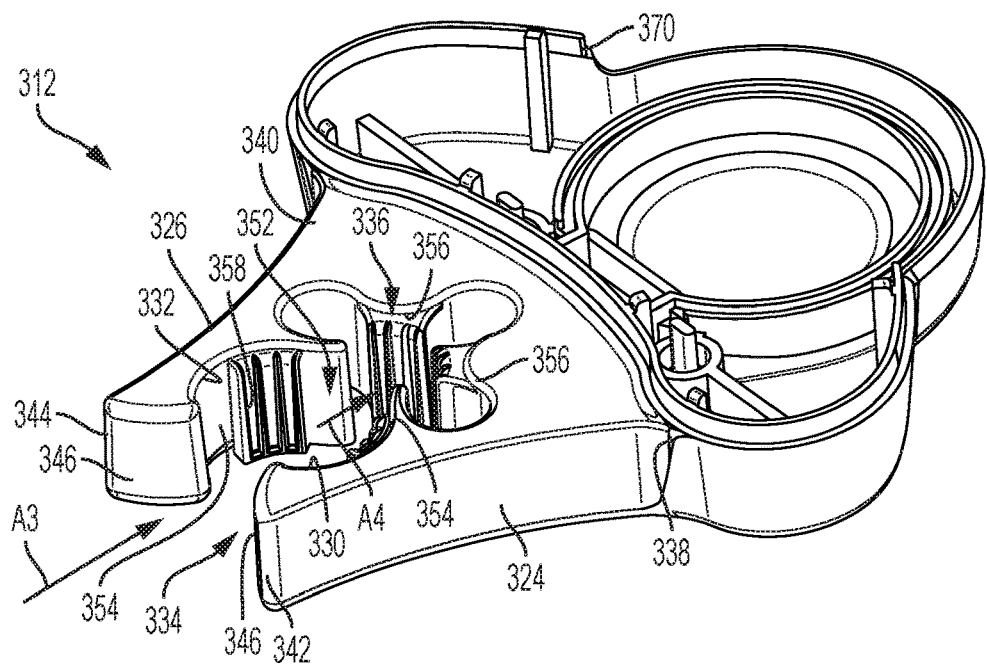
FIG. 16 is a perspective view of the base of the surgical tool cleaning device of FIG. 13.
Figure 17:
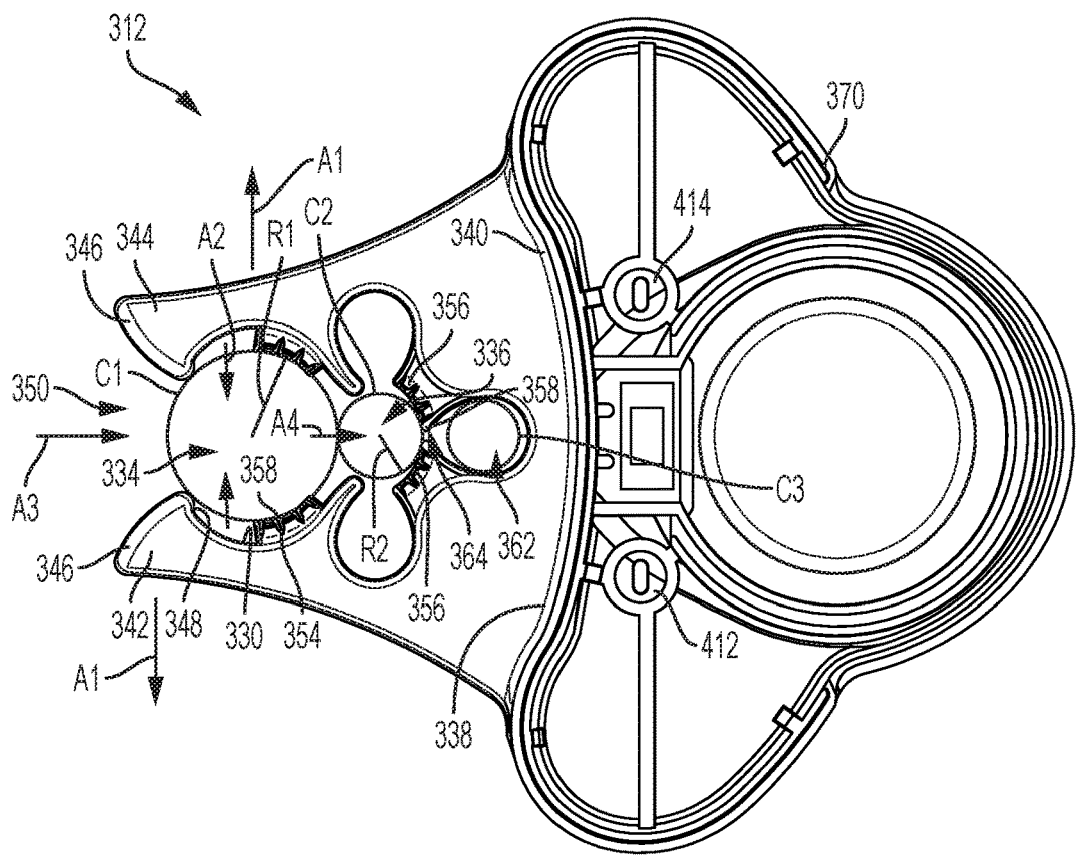
FIG. 17 is a top view of the base of the surgical tool cleaning device of FIG. 13.

With reference to FIGS. 14 and 15, in some examples, the housing 314 further includes a tubular fluid reservoir 380 enclosed by the cover 372 and/or the base 370. The tubular reservoir 380 is sized to receive a portion of the scope for cleaning and defogging the scope. In some examples, the reservoir is about 35 mm to 45 mm tall and has an outer diameter of about 15 mm to 25 mm. The fluid reservoir 380 can include an open top 382 accessible through the at least one opening 316 of the cover 372 and a closed bottom 384 mounted to the base 370. The fluid reservoir 380 defines an interior 386, configured to receive cleaning solution to clean the scope. The at least one sponge 320 can be inserted into the interior 386 of the fluid reservoir 380. The sponge 320 can be a circular shape and sized such that a peripheral edge 321 of the sponge 320 engages an inner surface 388 of the fluid reservoir 380 by a frictional engagement to hold the sponge 320 in place in the fluid reservoir 380.

As in previous embodiments, the heater assembly 322 is positioned in proximity to the fluid reservoir 380 and is configured to heat fluid and the sponge 320 contained therein. By heating the fluid and sponge to an appropriate temperature, the fluid effectively defogs a lens of the surgical scope, which improves a quality of images captured by the scope during a surgical procedure. Particularly, warming the lens of the scope to approximately body temperature reduces a likelihood that a lens of the scope will fog when it is inserted into the patient's body.

In some examples, the heater assembly 322 includes a conductive film 390 wrapped around at least a portion of an outer surface 392 of the fluid reservoir 380. The conductive film 390 can be any suitable conductive material, which increases in temperature when an electric current passes through the conductive film 390. Exemplary conductive materials include metallic films, such as films formed from copper, zinc, and similar materials. The conductive film 390 may also be a film formed from a conductive polymer material and/or a polymer film impregnated with conductive metallic particles. In other examples, the conductive film 390 can be replaced by other electrical circuitry for generating sufficient heat to warm the fluid reservoir 380 and surgical scope. For example, the heater assembly can include conductive wires, coils, foils, tape, or similar materials electrically connected to a power source for generating heat.

In some examples, the heater assembly 322 further includes an insulator 394 positioned around at least a portion of the conductive film 390 and the outer surface 392 of the fluid reservoir 380. For example, the insulator 394 can be an annular sleeve formed from an insulating material, such as silicone, neoprene, fiberglass, cotton, felt, or other insulating materials as are known in the art. In some examples, the insulator 394 can be molded or coated over the conductive film to provide protection for the film. In other examples, the insulator 394 is a separate sheet or sleeve wrapped around or positioned over the conductive film.

In some examples, the heater assembly 322 also includes a thermostat 396 electrically connected to a power source 410. The thermostat 396 can be configured to selectively apply power from the power source 410 to the conductive film 390, thereby causing the conductive film 390 to increase or decrease in temperature. The thermostat 396 can be mounted to other portions of the fluid reservoir 380 or at any other convenient location within the housing 314. In some examples, the thermostat 396 is configured to disconnect the power source 410 from the conductive film 390 when the thermostat 396 measures that the conductive film 390 and/or portions of the fluid reservoir 380 are above a target temperature value.

In some examples, the power source 410 includes battery terminals, such as a first battery terminal 412 and a second battery terminal 414, sized to receive one or more batteries 416. The batteries 416 can be conventional commercially available batteries, such as one or more of single A batteries, AA batteries, and/or a AAA batteries. For example, as shown in FIG. 14, the scope cleaner device 310 including two AA batteries 416. The battery terminals 412, 414 can be mounted to the base 370 of the housing 314 and configured to hold the batteries 416 in a position, in which a longitudinal axis L3 (shown in FIG. 14) of the battery 416 is parallel or is substantially parallel to a central longitudinal axis L1 (shown in FIG. 18) of a portion of the trocar received by the connector 312.

In some examples, the fluid reservoir 380 also includes an annular seal 398 connected to the open top 382 of the fluid reservoir 380. The annular seal 398 can be an elastomeric seal sized to receive the surgical device, such as the surgical scope, and to seal against a portion of the device to prevent fluid, such as defogging solution, from leaking from the interior 386 of the fluid reservoir 380. In some examples, the annular seal 398 includes a conical outer surface 391 extending radially inwardly from a peripheral edge 393 of the seal 398 to a narrow central opening 395. The annular seal 398 serves several purposes. First, it helps to maintain fluid in the fluid reservoir 380 by, for example, wiping excess fluid from the scope cleaner. The seal 398 also helps to prevent fluid from spilling out of the fluid reservoir 380 if the trocar, to which the cleaning device 310 is attached, is bumped, jostled, or moved. The seal 398 and central opening 395 can also be sized to facilitate filling the fluid reservoir 380 with defogging fluid. For example, a tip of a fluid bottle can be inserted into the interior 386 of the fluid reservoir 380 through the narrow opening 395. A top portion of the fluid bottle could rest against the conical surface 391 as the fluid reservoir 380 is being filled.

Cleaning Device with Integral Trocar

With reference to FIGS. 20-24, according to another embodiment, a cleaning device 510 is integrally formed with and supported by a trocar 512. For example, the combination cleaning device 510 and trocar 512 could be a disposable medical device configured for single use during a medical procedure. Once the procedure is completed, the device 510 and integral trocar 512 can be removed from the patient and discarded. Accordingly, the cleaning device 510 and trocar 512 may be manufactured from inexpensive disposable materials, such as injection molded plastics. Exemplary biocompatible plastic materials, which can be used for forming portions of the cleaning device 510 and trocar 512 can include, for example, polyesters, co-polyesters, polyethylene terephthalate (PET), polystyrene, high-density polyethylene, polycarbonate, and combinations thereof.

As in previous examples, the cleaning device 510 is configured for cleaning a surgical tool, such as a surgical scope, prior to insertion of the tool into a body of a patient during minimally invasive surgery. The cleaning device 510 includes the trocar 512, which includes a first end 514 configured to remain external to the patient's body, a second end 516 configured for insertion into the patient's body, and a sidewall 518 extending therebetween. The sidewall 518 can include structural features or texturing, which can make the trocar 512 easier to hold and manipulate during use. For example, a series of ridges and/or rings 520 can be molded into and extend from the sidewall 518. The trocar 512 is sized to receive surgical tools commonly used during minimally invasive surgical procedures. For example, the trocar 512 can have a minimum diameter D4 ranging from about 4.0 cm to 8.0 cm. The device 510 can be any length L4, such as about 10 cm to 20 cm.

The cleaning device 510 also includes an external cleaning portion 522, which remains external to the patient's body throughout the surgical procedure, and which is supported by the trocar 512. The cleaning portion 522 can be positioned near the proximal or first end 514 of the trocar 512. The cleaning portion 522 can include: a housing 524, at least a portion of which is integral with the sidewall 518 of the trocar 512; a fluid container 526 accessible through at least one opening 528 of the housing 524; and a heater assembly, generally indicated by 530 (shown in FIGS. 23 and 24), for warming a fluid in the container 526. The at least one first opening 528 of the housing 524 can be sized such that a lens of the surgical tool can be inserted through the opening 528 into the fluid container 526 to contact fluid, such as cleaning solution, in the fluid container 526. The housing 524 can be a rigid structure formed, for example, from the same injection molded plastic as the trocar 512 or from another material. The housing 524 can be integrally connected to and extend from a portion of the sidewall 518 of the trocar 512. The fluid container 526 and heating assembly 530 can be similar in size and function to any of the fluid reservoirs and heating assemblies previously described. Generally, the fluid container 526 is a tubular body positioned in an interior of the housing 524 having an open top end 532 accessible through the opening 528 of the housing 524 and a closed bottom 534 (shown in FIG. 23).

In some examples, the cleaning portion 522 further includes a surgical tool insertion or access portion 542 integral with and extending from the proximal or first end 514 of the trocar 512. The access portion 542 is accessible through at least one second opening 544 of the housing 524. The access portion 542 can include or define a funnel or funnel-shaped surface 546 extending from the at least one second opening 544 of the housing 524 to a narrow second end 548 (shown in FIG. 23) integral with and extending from the first end 514 of the trocar 512. In use, a practitioner, such as a surgeon, inserts the surgical tool into a channel or lumen of the trocar 512 through the access portion 542 of the device 510.

Figure 21:
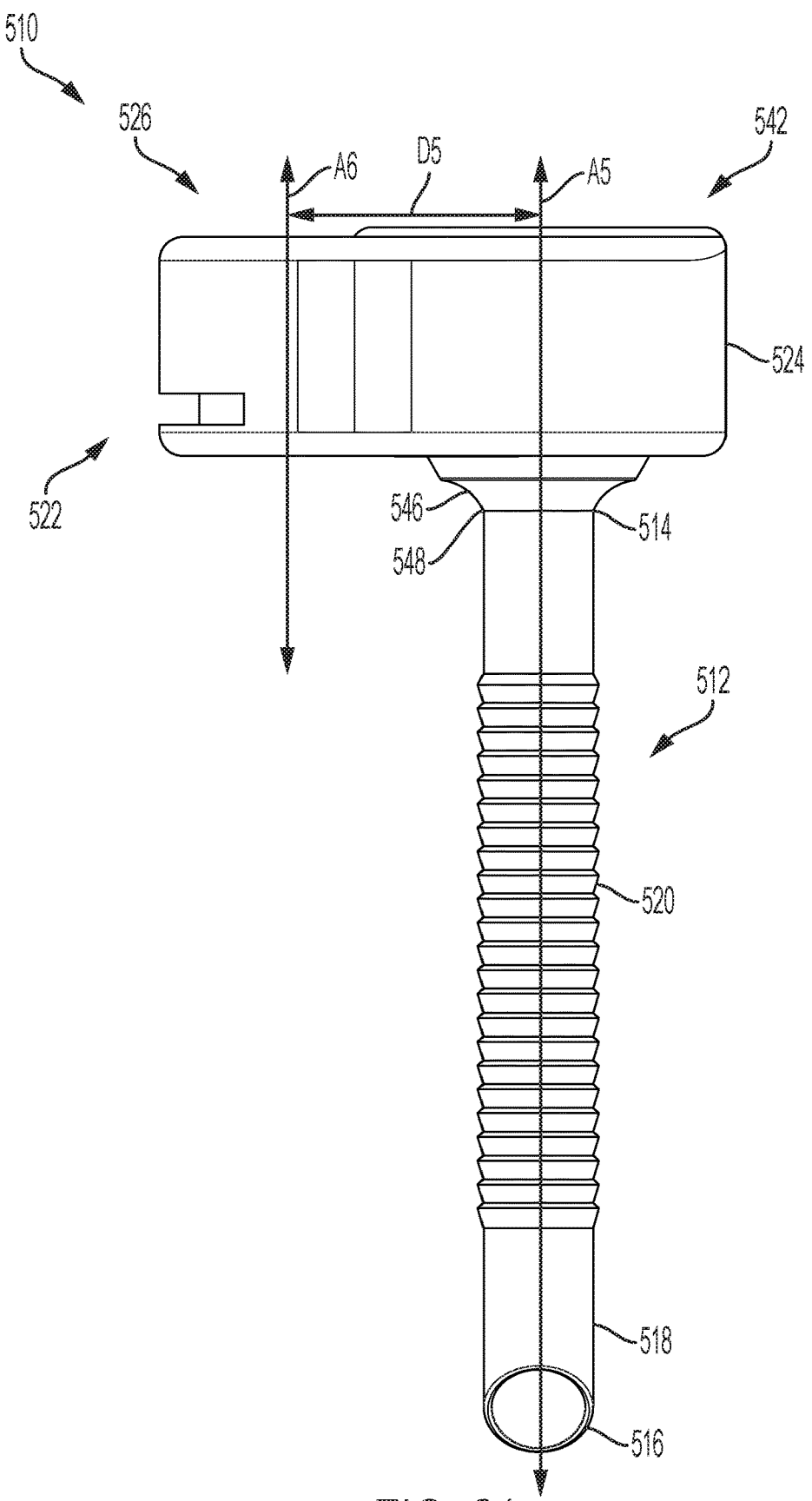
FIG. 21 is a front view of the surgical tool cleaning device and trocar of FIG. 20.

The housing 524 can be arranged so that both the at least one first opening 528 for accessing the fluid container 526 and the at least one second opening 544 for accessing the trocar 512 are easily accessible without needing to reposition the cleaning device 510 or trocar 512 during use. In order to ensure that both openings 528, 544 remain accessible for the practitioner during a procedure, as shown in FIG. 21, a central longitudinal axis A5 of trocar 512 can spaced apart from a central longitudinal axis A6 of the fluid container 526 by a fixed distance D5. Since the fluid container 526 and trocar 512 are spaced apart by the fixed distance, both openings 528, 544 remain accessible throughout the procedure. For example, the practitioner could insert the surgical tool into the fluid container 526 to clean the tool and then, immediately and without changing a position of the cleaning device 410 or trocar 412, insert the surgical into the trocar 512 through the access portion 542 to obtain images of the patient's body and/or to perform other minimally invasive tasks.

Figure 22:
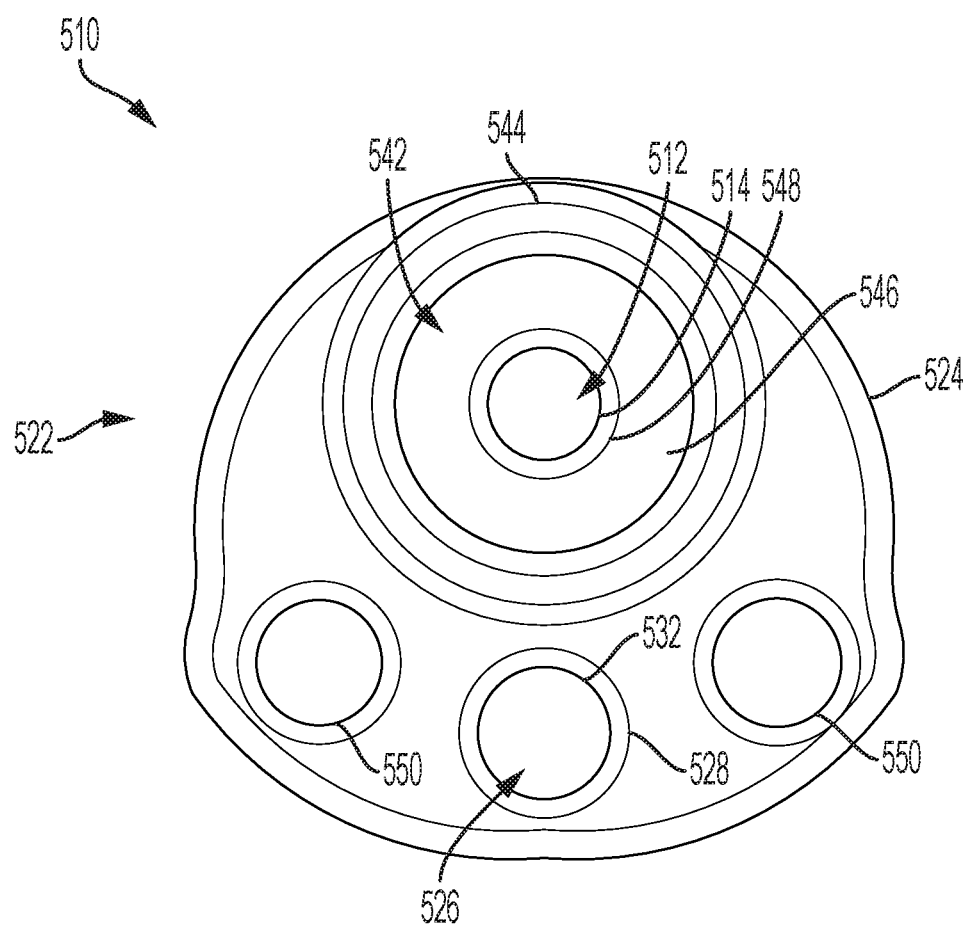
FIG. 22 is a top view of the surgical tool cleaning device and trocar of FIG. 20.
Figure 23:
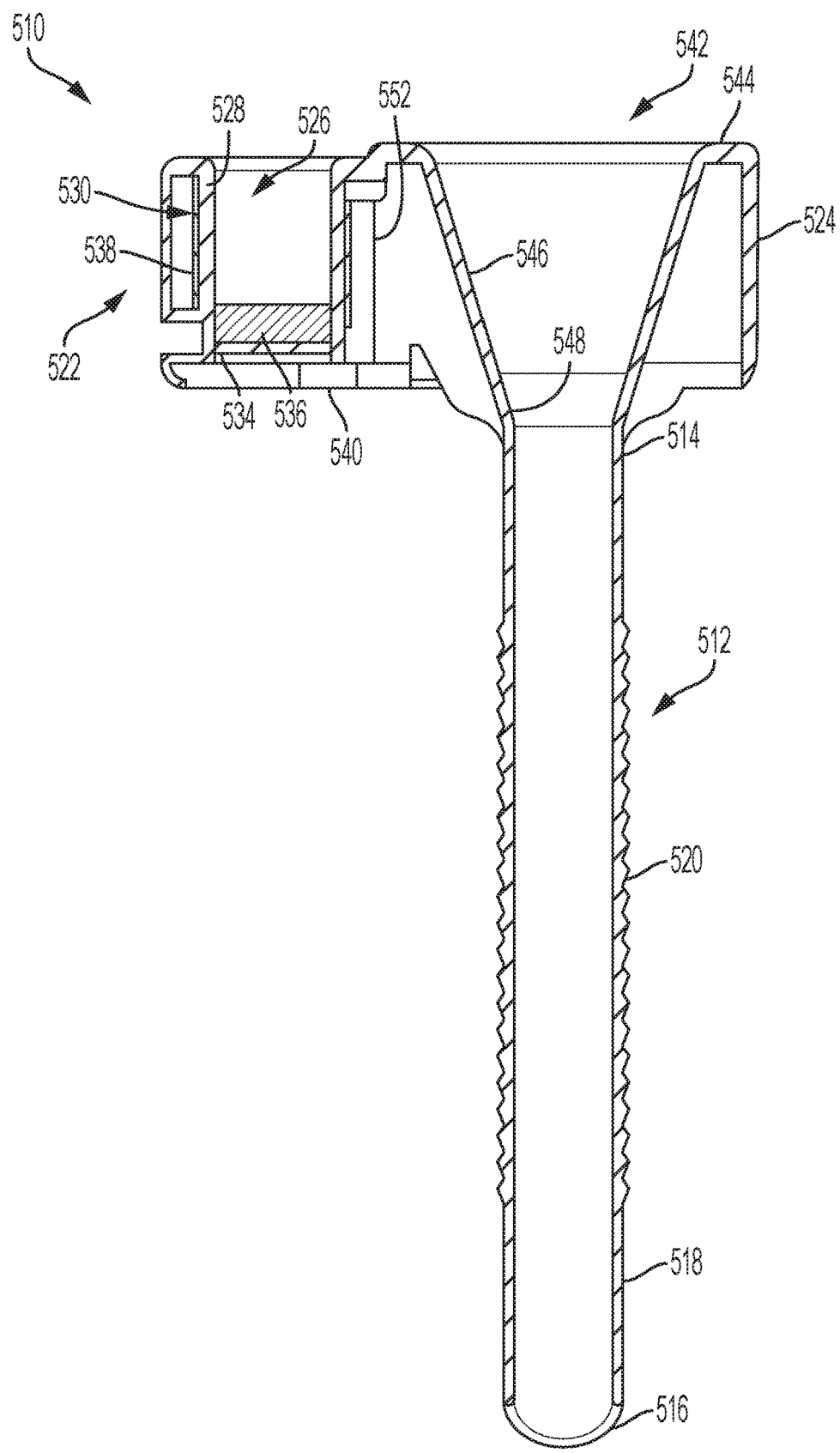
FIG. 23 is a front cross-section view of the surgical tool cleaning device and trocar of FIG. 20.

The cleaning device 510 can also include at least one cloth wiping element, such as a microfiber pad 550, adhered to a portion of an outer surface of the housing 524 for wiping fluid from a lens of the surgical tool. For example, as shown in FIG. 22, the housing 524 includes two pads 550 positioned on opposite sides of the first opening 528. Since the pads 550 are in close proximity to the opening 528, the practitioner can easily remove the surgical tool from the fluid container 526, wipe off any excess fluid using one of the pads 550, and then insert the surgical tool into the trocar 512 through the access port 542.

As in previous examples, the cleaning device 510 can include a sponge 536 (shown in FIGS. 23 and 24) disposed in an interior of the container 526. For example, the sponge 536 can be disk shaped and can be retained in the fluid container 526 by, for example, a frictional engagement between an inner sidewall of the fluid container 526 and an outer annular surface of the sponge 536. The heater assembly 530 can include any of the heater assemblies described previously, or any combinations thereof. For example, the heater assembly 530 can include a conductive foil 538 or coiled wire positioned around the fluid container 526. The conductive foil 538 or wire can be connected to a power source, such as battery terminals 540. In other examples, the heater assembly 530 can include chemical components that react to produce heat.

Figure 24:
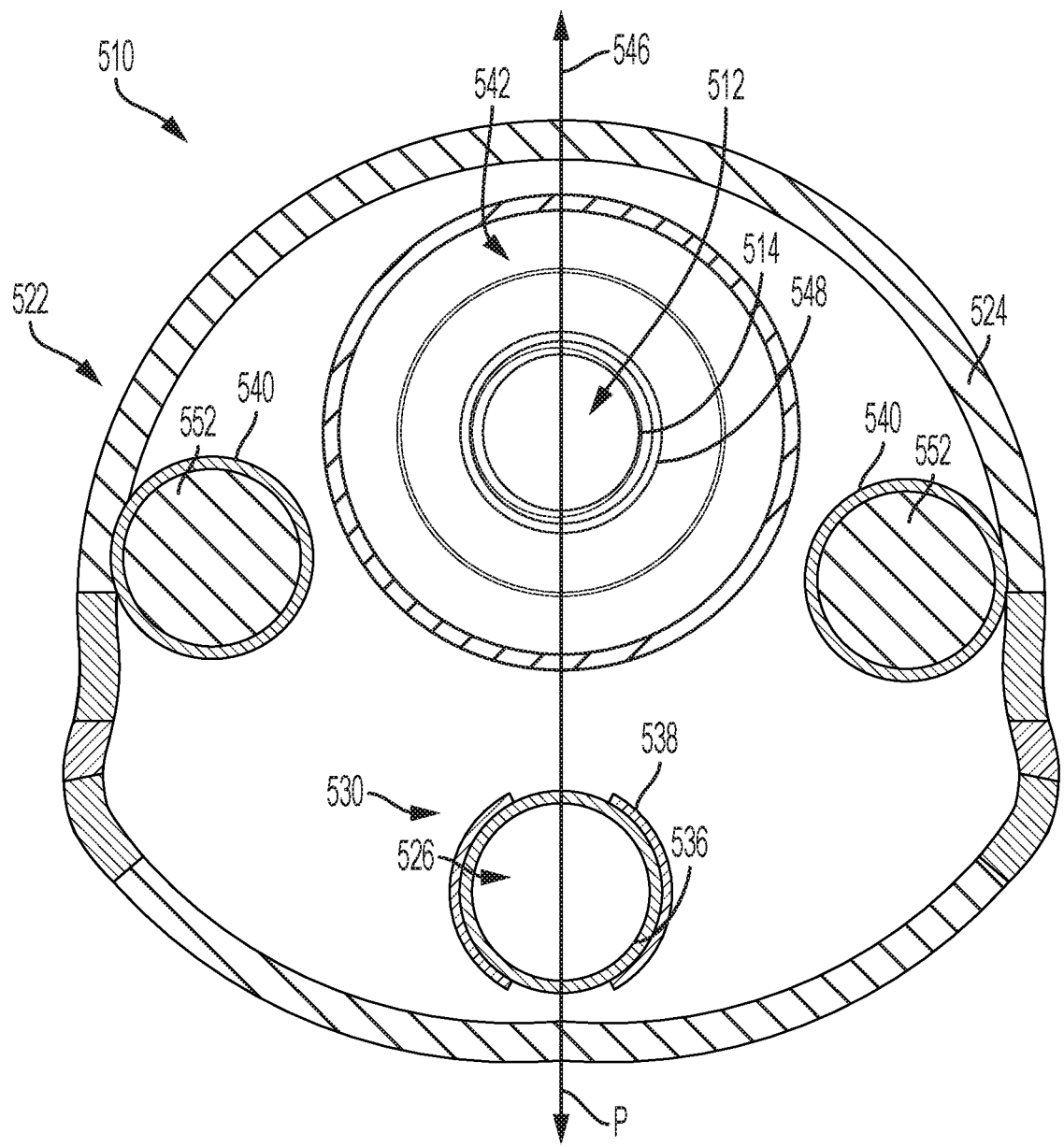
FIG. 24 is a top cross-sectional view of the surgical tool cleaning device and trocar of FIG. 20.

As shown in FIG. 24, the battery terminal(s) 540 are positioned in the interior of the housing 524, for example, between the fluid container 526 and the access port 542. Generally, the housing 524 is designed to be as small as possible, so as not to obstruct the practitioner's view of the patient and/or surgical access site. Accordingly, the battery terminal(s) 540 should be positioned in the housing to minimize a total volume of the housing 524 (e.g., positioned as close to the fluid container 526 and/or trocar 512 as possible). As shown in FIG. 24, the cleaning device 510 can include two battery terminals 540 and batteries 552 connected thereto, positioned on opposite sides of the device housing 524. For example, the batteries 552 can be held in a substantially vertical orientation, in which a longitudinal axis of the batteries 552 is parallel to the axis A5, A6 (shown in FIG. 21) of the fluid container 526 and/or trocar 512. The batteries 552 can be any standard battery size and shape, as are known in the art. For example, the batteries 552 can be size AA, AAA, C, and/or D, as well as various watch or button cell battery sizes. In some examples, the battery terminals 540 are equidistant from the fluid container 526 and/or access portion 542 of the device 510. In this arrangement, the housing 524 can be symmetrical along a plane P passing through the fluid container 526 and/or trocar 512. Other arrangements of battery terminals 540 and batteries 552 can also be used in order so that the trocar 512 and cleaning portion 522 are an appropriate size and shape for a specific medical procedure.

It is to be understood that the invention may assume various alternative variations, except where expressly specified to the contrary. It is also to be understood that the specific devices illustrated in the attached drawings, and described in the specification, are simply exemplary embodiments of the invention. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope thereof. For example, it is to be understood that the present invention contemplates that, to the extent possible, one or more features of any embodiment can be combined with one or more features of any other embodiment. The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A cleaning device configured for cleaning a surgical tool prior to insertion of the tool into a body of a patient during minimally invasive surgery, the cleaning device comprising: a housing comprising at least one opening for accessing an interior of the housing; a sponge and a heater assembly positioned in the interior of the housing; and a connector comprising a first arm and a second arm extending from an outer surface of the housing, wherein an inner surface of the first arm and an inner surface of the second arm comprise an outer portion defining at least a first recess sized to receive a sidewall of a first tubular body having a first diameter, and an inner portion defining a second recess sized to receive a sidewall of a second tubular body having a second diameter, smaller than the first diameter, and wherein the connector is configured to removably attach the housing to the sidewall of the first tubular body or to the sidewall of the second tubular body, thereby supporting the housing relative to the first tubular body or the second tubular body.

2. The cleaning device of claim 1, wherein the tubular body comprises a tubular portion of a surgical trocar.

3. The cleaning device of claim 1, wherein the connector supports the housing, such that a central longitudinal axis of a portion of the first tubular body received within the first recess or of the second tubular body received within the second recess of the connector is spaced apart from the interior of the housing.

4. The cleaning device of claim 1, wherein the connector supports the housing, such that a line normal to a bottom surface and passing through the opening of the housing is parallel to and a fixed distance from a central longitudinal axis of the portion of the first tubular body received within the first recess or of the second tubular body received within the second recess of the connector.

5. The cleaning device of claim 1, wherein the at least one opening is sized such that a lens of the surgical tool can be inserted through the at least one opening to access the sponge and/or the heater assembly.

6. The cleaning device of claim 1, wherein the first arm and the second arm of the connector are configured to deflect radially outwardly from the first recess and/or the second recess to receive the first or second tubular body and to move radially inwardly to engage a portion of a sidewall of the first or second tubular body upon insertion of the tubular body into the first recess and/or the second recess.

7. The cleaning device of claim 1, wherein the first arm and the second arm comprise a first end mounted to a portion of an outer surface of the housing and a free second end opposite the first end, the free second end comprising a protrusion comprising an inwardly angled outer surface configured to direct the sidewall of the first or second tubular body into the first recess and/or the second recess.

8. The cleaning device of claim 7, wherein an inwardly facing surface of the protrusion is configured to engage the sidewall of the first tubular body of the first diameter to maintain the first tubular body within the first recess.

9. The cleaning device of claim 7, wherein the first recess is accessible through a space between the protrusion of the first arm and the protrusion of the second arm, and wherein the second recess is accessible from the first recess through a space between portions of the first arm and the second arm other than the protrusions.

10. The cleaning device of claim 1, wherein the first diameter is from about 6.0 mm to 18.0 mm and the second diameter is from about 1.0 mm to 6.0 mm.

11. The cleaning device of claim 1, wherein an inner surface of the first arm and an inner surface of the second arm each comprise a first curved portion having a first radius sized such that the first curved portion engages a sidewall of the first tubular body, and a second curved portion having a radius sized such that the second curved portion engages a sidewall of the second tubular body.

12. The cleaning device of claim 1, wherein portions of the first arm and/or the second arm configured to contact a sidewall of the first tubular body and/or the second tubular body comprise textured regions configured to enhance a frictional engagement between the sidewall of the tubular body and the inner surface of the first arm and/or the second arm.

13. The cleaning device of claim 12, wherein the textured regions comprise a plurality of longitudinally extending ribs extending radially inwardly from inner surfaces of the first arm and/or the second arm.

14. The cleaning device of claim 1, further comprising a cloth wiping element adhered to a portion of an outer surface of the housing for wiping fluid from a lens of the surgical tool.

15. The cleaning device of claim 1, wherein the housing comprises:
a base integrally formed with the connector;
a cover comprising an open bottom connected to the base, a partially closed top, and an annular sidewall extending therebetween, wherein the at least one opening of the housing extends through the top of the cover; and
a tubular fluid reservoir comprising an open top accessible through the at least one opening of the cover and a closed bottom mounted to the base.

16. The cleaning device of claim 15, wherein the heater assembly comprises a conductive film wrapped around at least a portion of a sidewall of the fluid reservoir; an insulating film wrapped around at least a portion of the conductive film of the conductive film; and a thermostat electrically connected between the conductive film and a power source, configured to disconnect the conductive film from the power source when the thermostat measures a temperature above a target value.

17. The cleaning device of claim 15, wherein the base further comprises at least one battery terminal, configured to receive at least one battery for powering the heater assembly, and wherein the battery terminal holds the battery in a position, in which a longitudinal axis of the battery is parallel to a longitudinal axis of a portion of the tubular body received by the connector.

18. The cleaning device of claim 1, wherein the connector is symmetrical about a central axis, and wherein the central axis of the connector passes through the first recess and the second recess.

19. A cleaning device configured for cleaning a surgical tool prior to insertion of the tool into a body of a patient during minimally invasive surgery, the cleaning device comprising:
a housing comprising at least one opening for accessing an interior of the housing;
a sponge and a heater assembly positioned in the interior of the housing; and
a connector comprising a first arm and a second arm extending from an outer surface of the housing,
wherein an inner surface of the first arm and an inner surface of the second arm define at least a first recess sized to receive a sidewall of a first tubular body having a first diameter, and a second recess sized to receive a sidewall of a second tubular body having a second diameter, different than the first diameter,
wherein the connector is configured to removably attach the housing to the sidewall of the first tubular body or to the sidewall of the second tubular body, thereby supporting the housing relative to the first tubular body or the second tubular body, and
wherein the first arm and/or the second arm further define at least one third recess sized to receive and engage a sidewall of a third tubular body having a third diameter, which is less than the first diameter or the second diameter, and wherein the third recess is accessible through a space between the inner surface of the first arm and the inner surface of the second arm which forms a portion of the second recess.

20. A trocar assembly for introducing a surgical scope to a body during a minimally invasive surgery, the assembly comprising: a trocar comprising a tubular body comprising a sidewall having a first maximum outer diameter; and a cleaning device configured to removably mount to the sidewall of the tubular body of the trocar, the cleaning device comprising: a housing comprising at least one opening for accessing an interior of the housing; a sponge and a heater assembly positioned in the interior of the housing; and a connector comprising a first arm and a second arm extending from an outer surface of the housing, wherein an inner surface of the first arm and an inner surface of the second arm comprise an outer portion defining at least a first recess sized to receive the sidewall of the tubular body of the trocar, and an inner portion defining a second recess sized to receive a sidewall of a tubular body of a trocar having a second diameter which is smaller than the first diameter, and wherein the connector is configured to removably attach the housing to the trocar to support the housing relative to the trocar.

\* \* \* \* \*

UNITED STATES PATENT AND TRADEMARK OFFICE
CERTIFICATE OF CORRECTION

PATENT NO. : 10,881,284 B2
APPLICATION NO. : 16/288914
DATED : January 5, 2021
INVENTOR(S) : Claude Fiset It is certified that error appears in the above-identified patent and that said Letters Patent is hereby corrected as shown below:

In the Claims

Column 24, Line 3, Claim 16, delete "of the conductive film of the conductive;" and insert -- of the conductive film; --

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*